(12) United States Patent
Kanda

(10) Patent No.: US 7,417,734 B2
(45) Date of Patent: Aug. 26, 2008

(54) SYSTEM AND PROCESS FOR SORTING BIOLOGICAL PARTICLES

(75) Inventor: Masahiko Kanda, Hyogo (JP)

(73) Assignee: Bay Bioscience Kabushiki Kaisha, Hyogo (JP)

( * ) Notice: Subject to any disclaimer, the term of this patent is extended or adjusted under 35 U.S.C. 154(b) by 115 days.

(21) Appl. No.: 11/587,568

(22) PCT Filed: Apr. 28, 2005

(86) PCT No.: PCT/JP2005/008174

§ 371 (c)(1),
(2), (4) Date: Oct. 25, 2006

(87) PCT Pub. No.: WO2005/106427

PCT Pub. Date: Nov. 10, 2005

(65) Prior Publication Data

US 2007/0195310 A1     Aug. 23, 2007

(30) Foreign Application Priority Data

Apr. 30, 2004   (JP) ................ 2004-136099

(51) Int. Cl.
   *G01N 21/00*   (2006.01)
(52) U.S. Cl. .............. 356/337; 356/339; 356/343
(58) Field of Classification Search ............. 356/72, 356/73, 335–344
See application file for complete search history.

(56) References Cited

U.S. PATENT DOCUMENTS

| | | | |
|---|---|---|---|
| 3,579,721 A | * | 5/1971 | Kaltenbach ............ 425/3 |
| 3,826,364 A | * | 7/1974 | Bonner et al. ............ 209/3.1 |
| 4,050,077 A | * | 9/1977 | Yamada et al. ............ 347/75 |
| 4,487,320 A | * | 12/1984 | Auer ............ 209/3.1 |
| 4,498,766 A | | 2/1985 | Unterleitner |
| 4,545,677 A | | 10/1985 | Chupp |
| 4,981,580 A | | 1/1991 | Auer |

(Continued)

FOREIGN PATENT DOCUMENTS

EP     0121 262     10/1984

(Continued)

*Primary Examiner*—Gregory J. Toatley, Jr.
*Assistant Examiner*—Jarreas C Underwood
(74) *Attorney, Agent, or Firm*—Harness, Dickey & Pierce, P.L.C.

(57) ABSTRACT

A system which irradiates light onto a liquid flow containing a biological particle, detects the light therefrom to collect biological information thereon, and sorts the biological particle based upon the biological information, comprises an optical detector for detecting the light from the biological particle; an imaging device for imaging the flow and a droplet split off the flow; means for calculating, based upon the image taken by the imaging device, a distance from a detection point where the optical detector detects the light from the biological particle to a lower end position of the flow, and an interval between adjacent droplets split off the flow, thereby calculating a time that the particle moves from the detection point to the lower end position, based upon the distance and the interval; and means for providing the flow with electrons of a predetermined polarity depending upon the feature of the biological particle, when the calculated time passes after the optical detector detects the light from the biological particle. Thus, the structure of the system for sorting the biological particles can be simplified and the sorting accuracy can be improved.

7 Claims, 16 Drawing Sheets

U.S. PATENT DOCUMENTS 5,601,235 A * 2/1997 Booker et al. .................. 239/4
6,133,044 A * 10/2000 Van den Engh ............. 436/177
6,248,590 B1 * 6/2001 Malachowski ............... 436/63

FOREIGN PATENT DOCUMENTS

| JP | 49-109093 | 10/1974 |
| JP | 59-000643 | 1/1984 |
| JP | 59-184862 | 10/1984 |
| JP | 60-195436 | 10/1985 |
| JP | 6-288896 | 10/1994 |
| JP | 2002-505423 | 2/2002 |
| JP | 2003-503808 | 1/2003 |

* cited by examiner

SYSTEM AND PROCESS FOR SORTING BIOLOGICAL PARTICLES

TECHNICAL FIELD

The present invention relates to a system and a process for collecting biological information on biological particles such as cells and chromosomes and for sorting biological particles based upon the collected biological information. In particular, the present invention related to a flow cytometer or a cell sorter, forming a laminar flow containing cells or chromosomes dyed with pigment material such as fluorochrome, irradiating light such as laser beam on the laminar flow to detect information light (scattered light and fluorescent light), converting optical information within the information light into electrical signals to collect biological information on cells or chromosomes, and if desired, extracting a group of particular cells or chromosomes based upon the biological information.

BACKGROUND ART

As the biotechnology has been developed, a flow cytometer is more commonly used in the fields of medicine and biology for automatic analysis and fractionation of cells or chromosomes (which are collectively referred to as "cells"). The flow cytometer forms a stream of the analyte cells within a flow channel performing as cell aligning means, and irradiates laser beam on the stream of the cells to detect information light scattered/emitted at the cells (i.e., forward- and side-scattered light, and fluorescent light). Also, it converts the information light into electrical signals to analyze the cells based upon the electrical signals, allowing high throughput of analyzed cells and extraction (sorting) of a particular group of cells, if necessary.

FIG. 16 is a schematic view of the flow cytometer, for illustrating a typical structure and operation thereof. In the flow cytometer 200 shown in the drawing, a liquid suspension 201 containing cells received in a container and a sheath fluid 202 received in another container are each guided into a funnel-shaped flow chamber (nozzle) 204 by air pumps 203. Within the flow chamber 204, the sheath fluid 202 forms a cylindrical laminar flow, i.e., a sheath flow, encompassing the liquid suspension 201 therein, in which a discrete one of the cells runs one-by-one along the central axis of the flow chamber 204. As closer to the bottom end of the flow chamber 204, the sheath flow runs faster, in which a laser beam 207 is irradiated from a laser beam source 205 and focused by a collective lens 206. Most of the cells in the liquid suspension 201 are fluorescently labeled with fluorescent material such as a fluorescent pigment and a fluorescent-labeled monoclonal antibody. Therefore, irradiation of the laser beam onto the cells generates the scattered light and the fluorescent light.

The scattered light passes through collective optics including a collective lens 208 and a beam block 209 to an optical detector 210 such as a photodiode designed for detecting the scattered light. In the meanwhile, a red-based fluorescent light is received by means of an optical detector 215, through another collective optics including a collective lens 211, a half-mirror 212, a collective lens 213 and a filter 214, also a green-based fluorescent light is received by means of an optical detector 218, through the half-mirror 212, a collective lens 216 and a filter 217. Photomultiplier tubes are typically utilized as the fluorescent detectors 215, 218 capable of detecting faint fluorescent light. A signal processing circuitry 219 receives various signals output from the detector 210 for the scattered light, the detector 215 for the red-based fluorescent light and the detector 218 for the green-based fluorescent light, and analyzes strength of the scattered light and the fluorescent lights, thereby to identify the analyte cell.

As illustrated in FIG. 17, the identification result is transmitted from the signal processing circuitry 219 to an electron charger 220. The electron charger 220 charges the liquid suspension 201 and the sheath fluid 202 with electrons of a predetermined polarity in accordance with the identification result of the cells, just before the identified cell reaches the break-off point. 221 at the bottom end of the sheath flow and a droplet containing the identified cell is formed, i.e., just before the identified cell reaches break-off point at the bottom end of the sheath flow to be the droplet. As the result, the droplet split off the sheath flow at the break-off point 221 is charged with the electrons of the predetermined polarity. The charged droplet falling downwardly is attracted and deflected between a pair of electrodes 222, 223 which are provided beneath the break-off point 221 and applied with potential of different polarity, so that the droplet is sorted into one of the collection tubes 224, 225 which are arranged below the electrodes 222, 223. (See, for example, Patent References 1-4.)

Patent Reference 1: JP 59-000643, A
Patent Reference 2: JP 59-184862, A
Patent Reference 3: JP 60-195436, A
Patent Reference 4: JP 03-503808, A

DISCLOSURE OF INVENTION

Problems to be Solved by Invention

As above, in the flow cytometer, the level (or height) at which the cell is detected (detection point) is different from the level (or height) at which the detected cell is charged (charging point, break-off point). Therefore, before operating the flow cytometer, the distance between the detection point and the charging point has to precisely be measured, and be input as the characteristic value of the flow cytometer. However, the appropriate charging point varies based upon viscosity/temperature of the liquid (i.e., liquid suspension and sheath fluid), the condition of a jet nozzle and so on, thereby causing a disadvantage deteriorating accuracy of the sorting. A camera may be provided to measure the distance between the detection point and the charging point by shifting the camera upwardly and downwardly, however, a mechanism for shifting the camera vertically is required and also an extremely bothersome tasks are necessary for the measuring method thereof.

MEANS TO SOLVE THE PROBLEMS

To address the drawbacks, the present invention is to provide a system which irradiates light onto a liquid flow containing a biological particle, detects the light therefrom to collect biological information thereon, and sorts the biological particle based upon the biological information, the system comprising:

an optical detector for detecting the light from the biological particle;

an imaging device for imaging the flow and a droplet split off the flow;

means for calculating, based upon the image taken by the imaging device, a distance from a detection point where the optical detector detects the light from the biological particle to a lower end position of the flow, and an interval between adjacent droplets split off the flow, thereby calculating a time that the particle moves from the detection point to the lower end position, based upon the distance and the interval; and means for providing the flow with electrons of a predetermined polarity depending upon the feature of the biological particle, when the calculated time passes after the optical detector detects the light from the biological particle.

Another aspect of the present invention is to provide a system which sorts a biological particle in accordance with biological information thereof, comprising:

a path-defining structure which defines a liquid flow arranging a plurality of biological particles at a predetermined interval therein, and ejects the flow to form a droplet containing the biological particle;

an irradiator for irradiating light onto the biological particle contained in the flow;

a detector for detecting the light from the biological particle;

an imaging device for imaging the flow and a droplet split off the flow;

means for calculating, based upon the image taken by the imaging device, a distance from a detection point where the detector detects the light to a lower end position of the flow, and an interval between adjacent droplets split off the flow, thereby calculating a time that the particle moves from the detection point to the lower end position, based upon the distance and the interval;

a processor for collecting biological information on the biological particle from the light detected by the detector;

means for providing the flow with electrons of a predetermined polarity depending upon the biological information on the biological particle processed by the processor, when the calculated time passes after the optical detector detects the light from the biological particle; and means for deflecting a falling direction of the droplet containing the biological particle with use of the electrons provided with the biological particle.

Another aspect of the present invention is to provide a system which irradiates light onto a liquid flow containing a biological particle, detects the light therefrom to collect biological information thereon, and sorts the biological particle in accordance with the biological information, the system comprising:

an optical detector for detecting the light from the biological particle;

an oscillation generator for oscillating the flow;

an imaging device for imaging the flow and a droplet split off the flow;

means for detecting, based upon the image taken by the imaging device, size of a small droplet formed between a lower end position of the flow and one of the droplets closest thereto; and means for controlling an amplitude of the oscillation generated by the oscillation generator based upon the size of the small droplet.

The present invention is to provide a process for sorting a biological particle, the process including:

defining a liquid flow containing the biological particle;

irradiating light onto the biological particle contained in the liquid flow;

detecting the light from the biological particle;

collecting information on the biological particle based upon the detected light;

imaging the flow and a droplet split off the flow;

calculating, based upon the image of the flow, a distance from a detection point of the light to a lower end position of the flow, and an interval between adjacent droplets split off the flow, thereby calculating a time that the liquid and the particle move from the detection point to the lower end position, with use of the distance and the interval;

injecting electrons to the flow based upon the biological information on the biological particle, when the calculated time passes after the light from the biological particle is detected; and sorting the droplet split off the flow with use of the injected electrons.

Another aspect of the present invention is to provide a process for irradiating light onto a liquid flow containing a biological particle, detecting the light from the biological particle, collecting biological information on the biological particle, and sorting the biological particle in accordance with the collected biological information, the process including:

detecting the light from the biological particle;

imparting oscillation to the flow;

imaging the flow and a droplet split off the flow;

detecting size of a small droplet formed between a lower end position of the flow and the closest droplet based upon the image; and controlling an amplitude of the oscillation based upon the size of the small droplet.

ADVANTAGES OF INVENTION

According to the system and the process so embodied, the imaging means can be fixed. Therefore, the system can be simplified and the accuracy of the sorting of the biological particles can be improved.

BRIEF DESCRIPTION OF REFERENCE NUMERALS

1: system, 2: path-defining structure (flow-path block), 4: sheath flow, 5: irradiation device, 6: first laser generator, 7: second laser generator, 8: first laser beam, 9: fiber optics, 11: collective lens, 12: second laser beam, 13: fiber optics, 14: beam expander, 15: collective lens, 21: first detecting apparatus, 22: collective lens, 23: optical detector, 24: signal processor, 25: second detecting apparatus, 90: sorting device, 110: droplet controller, 112: stationary camera, 113: stroboscopic lamp, 114: video digitizer, 117: central controller, 118: oscillation generator driver, 119: stroboscopic-lamp driver, 120: charge driver, 121: drop-delay controller, 133: droplet, 134: satellite drop

BEST MODE FOR CARRYING OUT THE INVENTION

Referring to drawings, a flow cytometer will be described herein as one of embodiments of a system for collecting information on biological particles, according to the present invention.

Figure 1:
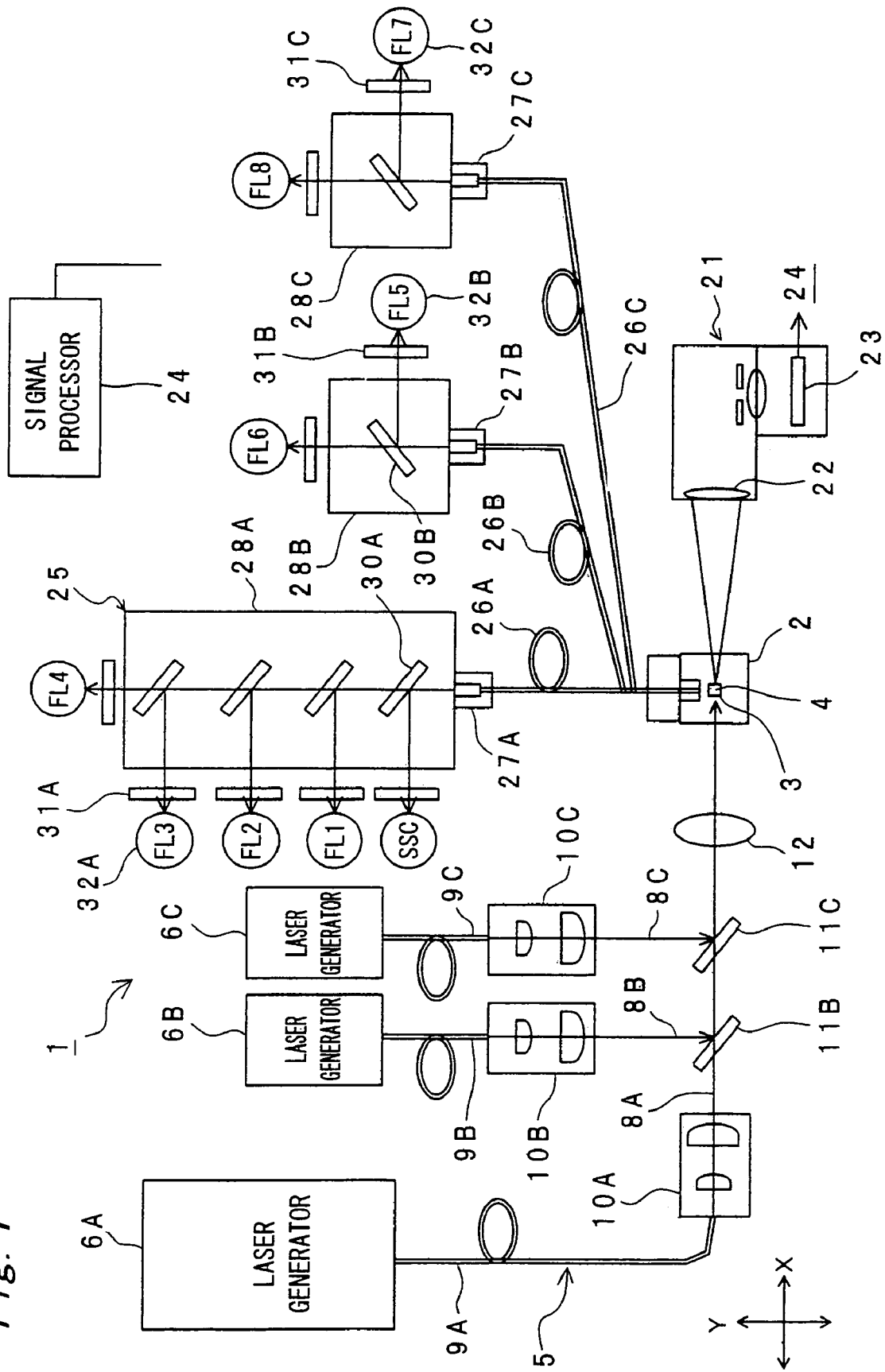
FIG. 1 is a schematic view illustrating optical elements of a system of the present invention.

I. Optical Components:

FIG. 1 illustrates several optical elements of the flow cytometer. As shown in FIG. 1, the flow cytometer 1 includes a flow-path block 2 (path-defining structure, see FIG. 2) for defining a thin flow path through which fluid is running. The fluid contains biological particles (cells or chromosomes) dyed with fluorescent pigment or fluorochrome antibody, typically consisting of fluid suspension containing cells and sheath fluid. An irradiation device 5 of the present invention includes a plurality of excitation light sources for irradiating light onto the sheath flow 4 running through the flow path 3 defined by the flow-path block 2. Preferably, laser-beam generators are utilized as the light sources for generating the laser beams having wavelengths different from one another. In the present embodiment, for instance, three of the excitation light sources are utilized, a first laser generator 6A is used as the first light source to generate a first laser beam having a wavelength of 488 nm (argon laser beam), a second laser generator 6B is used as the second light source to generate a second laser beam having a wavelength of 635 nm (helium-neon laser beam), and a third laser generator 6C is used as the third light source to generate a third laser beam having a wavelength of 375 nm (ultraviolet laser beam).

Also, the irradiation device 5 includes a plurality of fiber optics 9A-9C and beam expanders 10A-10C for guiding the 1st-3rd laser beams emitted from the 1st-3rd laser generators 6A-6C to the sheath flow 4. The laser beams emitted from the 1st-3rd laser generators 6A-6C are transmitted through the fiber optics 9A-9C, the beam expanders 10A-10C for adjusting the laser beams, two of the reflection/transmission mirrors 11B, 11C for combining the laser beams, and a single collective lens 12 for collecting the laser beams onto the sheath flow 4.

Figure 16:
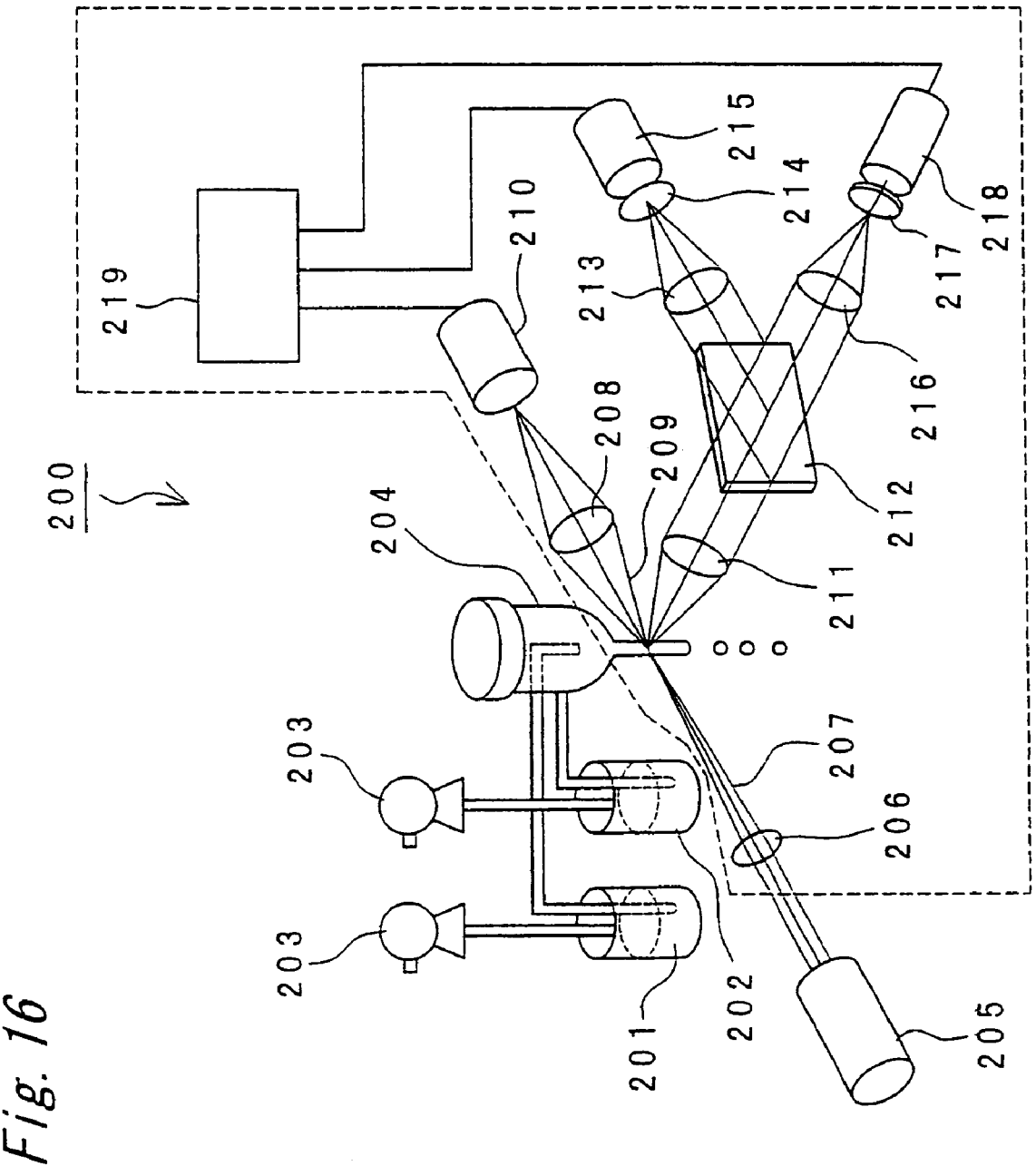
FIG. 16 is a perspective view of a conventional system for collecting biological features on the biological particles.
Figure 17:
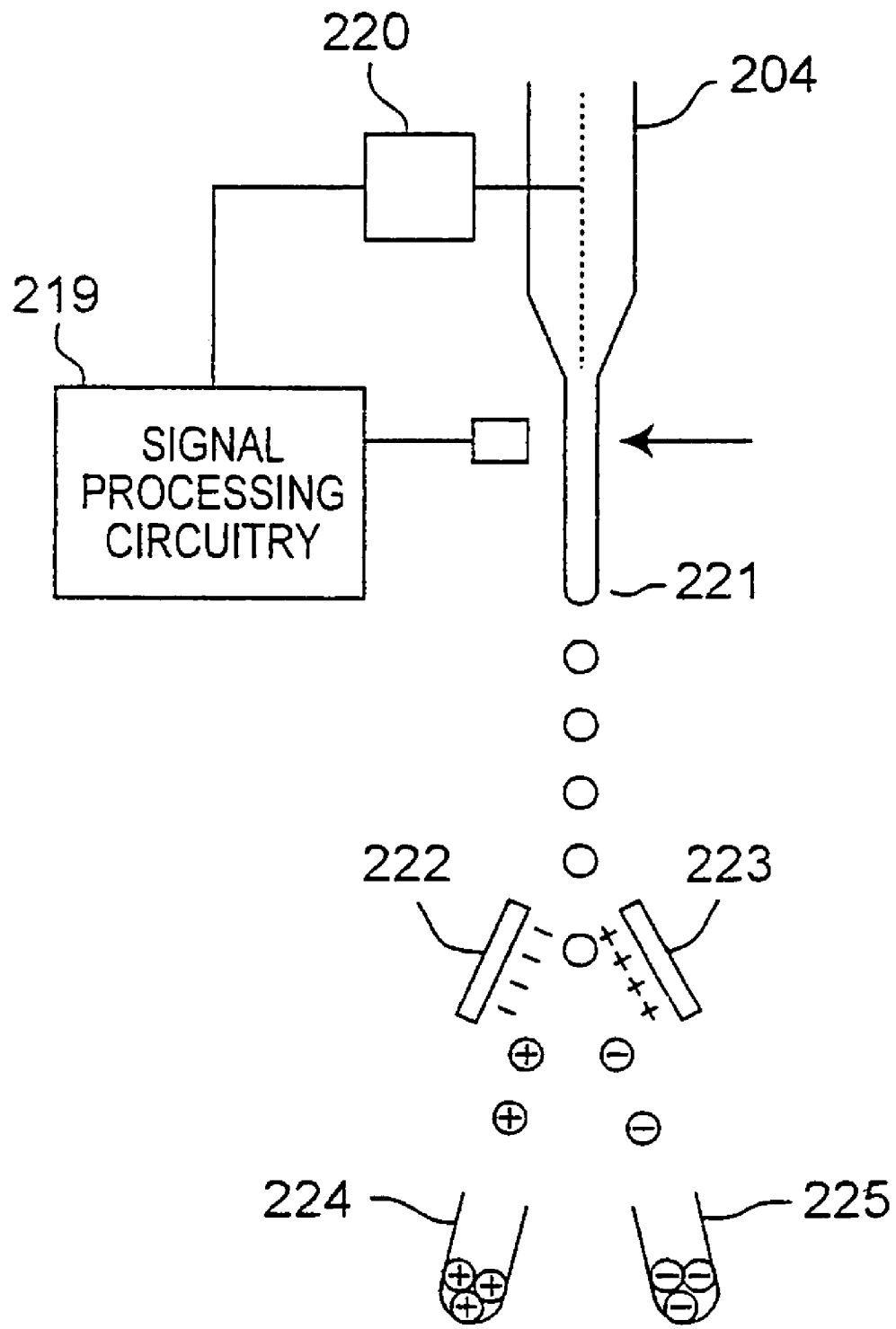
FIG. 17 is a schematic view illustrating the sorting of the biological particles.

Beyond the flow path block 2 in the direction of the incident laser beams, a first detecting apparatus 21 is arranged for detecting the forward-scattered light (information light) scattered by the particles running through the flow path in the flow-path block 2. Similar to the conventional flow cytometer as described with reference of FIG. 16, the first detecting apparatus 21 of the present invention includes a collective lens 22 and an optical detector 23 designed such that the forward-scattered light from the cell is focused by the collective lens 22 onto the optical detector 23. Also, the optical detector 23 is electrically connected with the signal processing apparatus 24 so that information detected by the optical detector 23 is transmitted to the signal processing apparatus 24 for processing the information therein. The details for processing the signals by the signal processing apparatus 24 will be described later. On the other hand, a second detecting apparatus 25 for detecting fluorescent/side-scattered light from the cells includes 1st-3rd fiber optics 26A-26C for receiving fluorescent/side-scattered light of the 1st-3rd laser beams 8A-8C, respectively. One ends of the 1st-3rd fiber optics 26A-26C are secured to respective positions corresponding to the collection levels of the 1st-3rd laser beams 8A-8C (see FIG. 4), respectively. Other ends of the fiber optics 26A-26C are optically connected with 1st-3rd spectrometers 28A-28C through the fiber optics 27A-27C, respectively.

The 1st-3rd spectrometers 28A-28C include one or more splitting filters (half-mirrors) 30A-30C for splitting light from the 1st-3rd fiber optics 26A-26C. Each of the splitting filters 30A-30C is provided with a function selectively reflecting or transmitting light having a predetermined range of wavelength. Also, a plurality of bandpass filters 31A-31C are provided downstream the splitting filters 30A-30C in the beam transmission directions, for selectively transmitting light of a predetermined waveband among light reflected or transmitted by each of the splitting filters. Further, a plurality of optical detectors 32A-32C (SSC, FL1-FL8) are provided downstream the bandpass filters 31A-31C in the beam transmission directions, for detecting optical information (side-scattering light and fluorescent light responsive to the predetermined fluorescent dye) of light transmitted through the bandpass filters.

According to the flow cytometer 1 so structured, the 1st-3rd laser beams 8A-8C generated by the 1st-3rd laser generators 6A-6C are transmitted through the fiber optics 9A-9C, the beam expanders 10A-10C, and the collective lens 12 collecting the beams onto the particles in the flow path 3 defined by the flow-path block 2. If the laser beams are collected with one collective lens 12 as illustrated in the drawing, the laser beams 8A-8C of wavelengths different from one another causes an axile chromatic aberration. Thus, according to the present embodiment, in order to eliminate the axile chromatic aberration due to the difference of the wavelengths, the beam expanders 10A-10C are used for slightly adjusting the laser beams 8A-8C, based upon the wavelengths of the 1st-3rd laser beams 8A-8C, to be non-parallel beams that should generally be parallel beams, and collects the adjusted laser beams onto the target positions.

The biological particles delivered by the sheath flow 4 are dyed with a plurality of predetermined fluorescent pigments or fluorochrome antibodies. The forward-scattering light that scatters in the forward direction parallel to the incident light is collected by the collective lens 22 of the first detecting apparatus 21 to enter the optical detector 23, which in turn reads optical information in the forward-scattering light for converting optical information to electrical signals. Also, the side-scattering light and the fluorescent light are each received by the 1st-3rd fiber optics 26A-26C of the second detecting apparatus 25 which is arranged on the side of the fluorescent light and the incident light. The laser beams received by the fiber optics 26A-26C are transmitted through the fiber connectors 27A-27C to the 1st-3rd detecting apparatuses 25A-25C. Then, the laser beams is split into a plurality of beams by means of the splitting filters 30A-30C, each of which enters the respective one of the bandpass filters 31A-31C for detection by the optical detectors 32A-32C. The optical detectors 32A-32C (SSC, FL1-FL8) detect only the beams having different waveband transmitting through the bandpass filters 31A-31C. As described above, the laser beams detected by the optical detectors 32A-32C are converted to the electrical signals in response to the information in the beams that is transmitted to the signal processing apparatus 24 for further signal processing. The processed signals are used for identifying the biological characteristics (feature) of the particles and for sorting the particles as will be described hereinafter.

Figure 2:
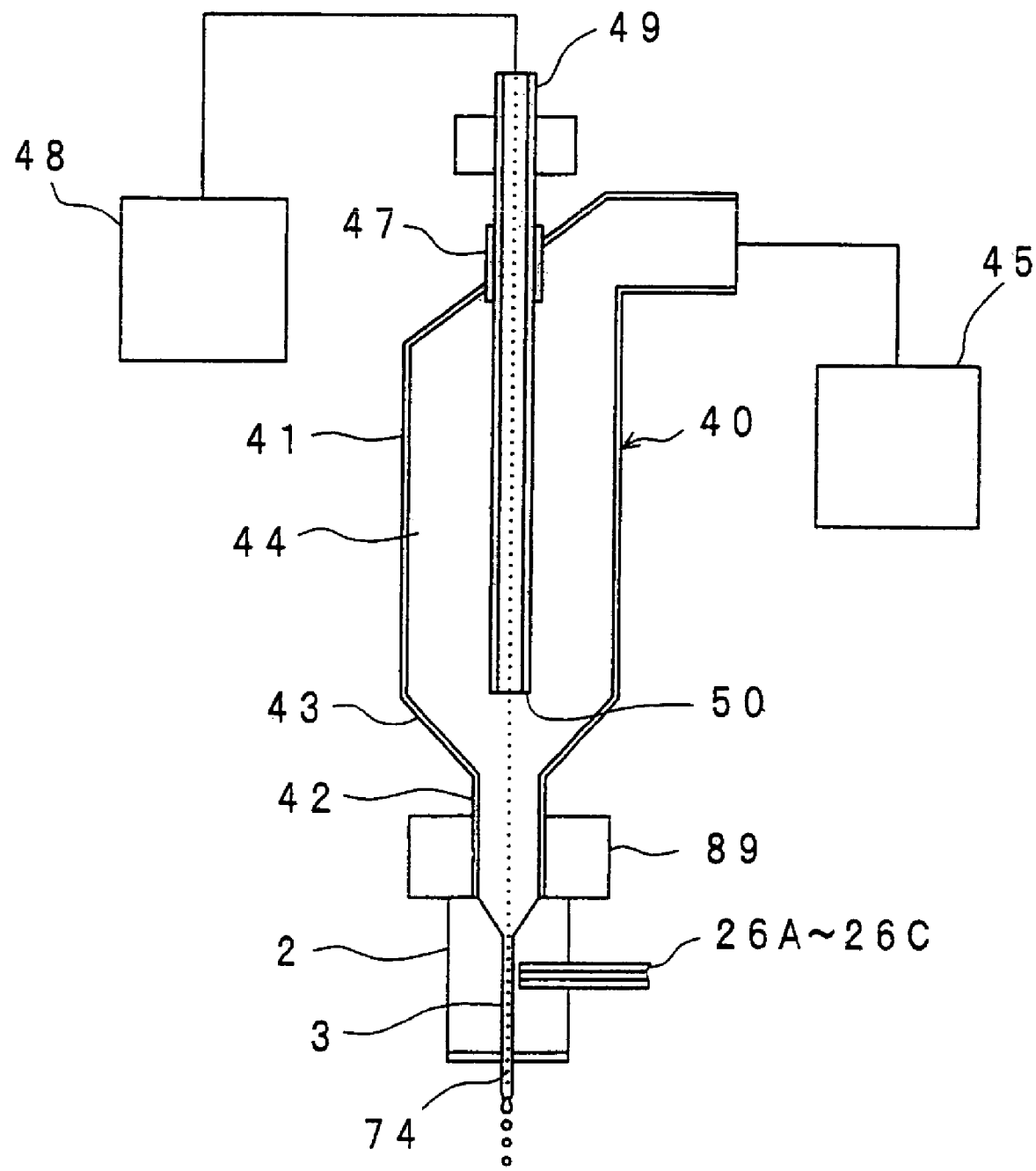
FIG. 2 is a side view illustrating a hydrodynamic structure of the system of the present invention.

II. Hydrodynamic Components:

The hydrodynamic components of the cytometer will be described herein. FIG. 2 is a schematic view illustrating a laminar-flow generating vessel 40 and the flow-path block 2 connected thereto at the bottom end. As shown in the drawing, the vessel 40 includes an upper large-diameter cylinder 41, a lower small-diameter cylinder 42, and a taper member 43 for connection between the large-diameter cylinder 41 and the small-diameter cylinder 42, which are all concentrically arranged, for defining a laminar-flow generating chamber 44 therein. The top end of the vessel 40 is connected to the sheath-fluid source 45. A tube capsule 47 that extends along the central axis of the vessel 40 is fixed on the ceiling of the vessel 40. Also, a suspension-fluid tube (sheath tube) 49 connected with the suspension-fluid source 48 is inserted into the tube capsule 47. The inner diameter of the tube capsule 47 and the outer diameter of the suspension-fluid-tube 49 are selected such that the suspension-fluid tube 49 can be slid along the tube capsule 47 and slightly inclined in relative to the tube capsule 47. Thus, while a nominal gap is defined between the tube capsule 47 and the suspension-fluid tube 49, an appropriate sealing member such as an O-ring made of rubber (not shown) seals the gap.

Figure 3:
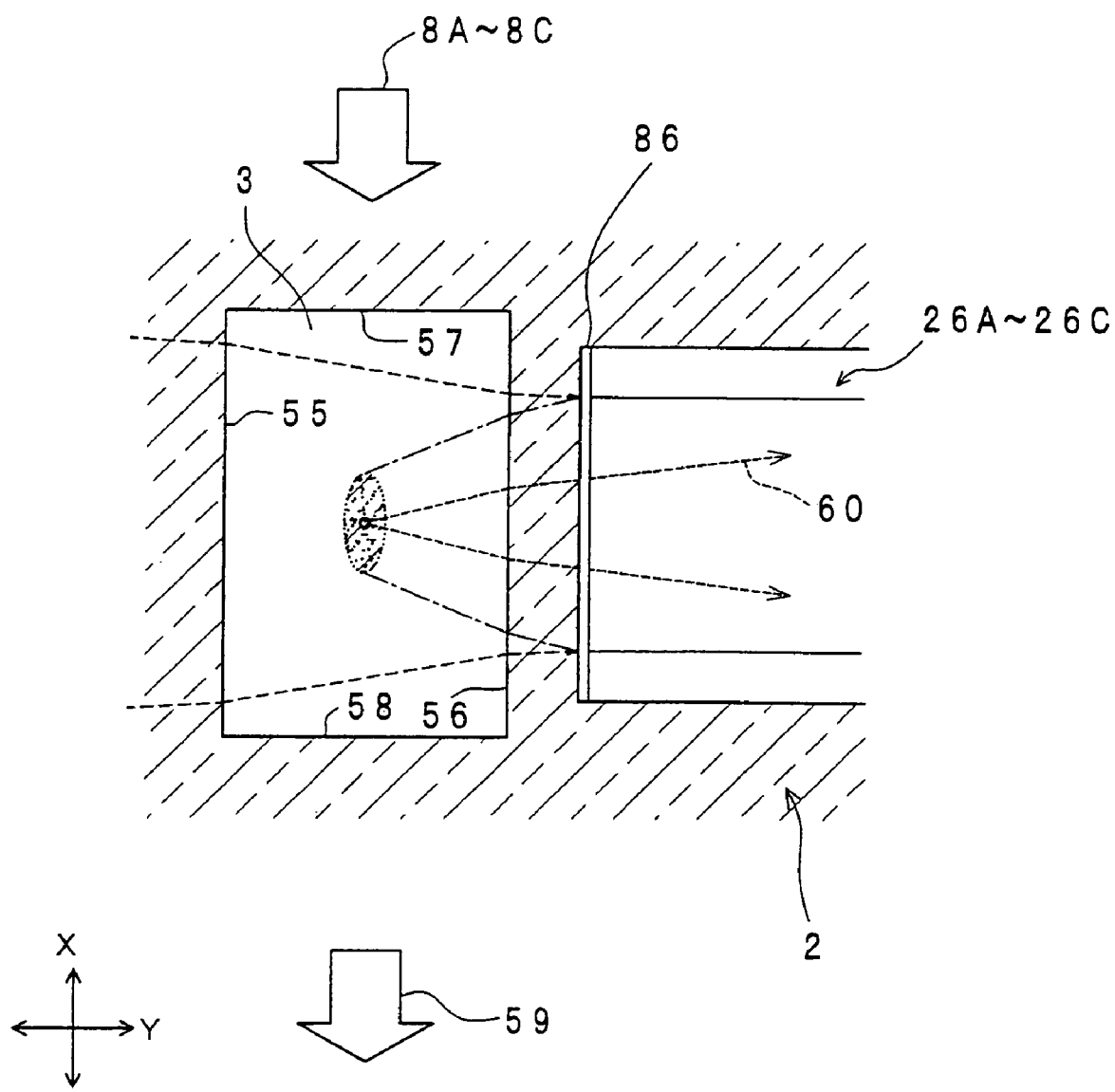
FIG. 3 is an enlarged cross sectional view of a detection flow path of the system of FIG. 1 and a portion of fiber optics arranged adjacent thereto.

The flow-path block 2 connected to the bottom end of the vessel 40 is made of transparent material selected from a group consisting of quartz, glass, fused silica, transparent plastic, etc. Also, the flow-path block 2 has a thin path flow 3 concentrically arranged with the central axis of the vessel 40. The flow-path block 2 defining the path flow 3 has a rectangular cross section including longitudinal walls 55, 56 extending along the X-direction and transverse walls 57, 58 extending along the Y-direction as shown in FIG. 3. Also, the flow-path block 2 is designed such that the 1st-3rd laser beams 8A-8C entering from one of the transverse walls 57 cause the forward-scattered light to be output through the opposing transverse wall 58 and the fluorescent/side-scattered light to be output through one of the longitudinal walls 56.

Figure 4:
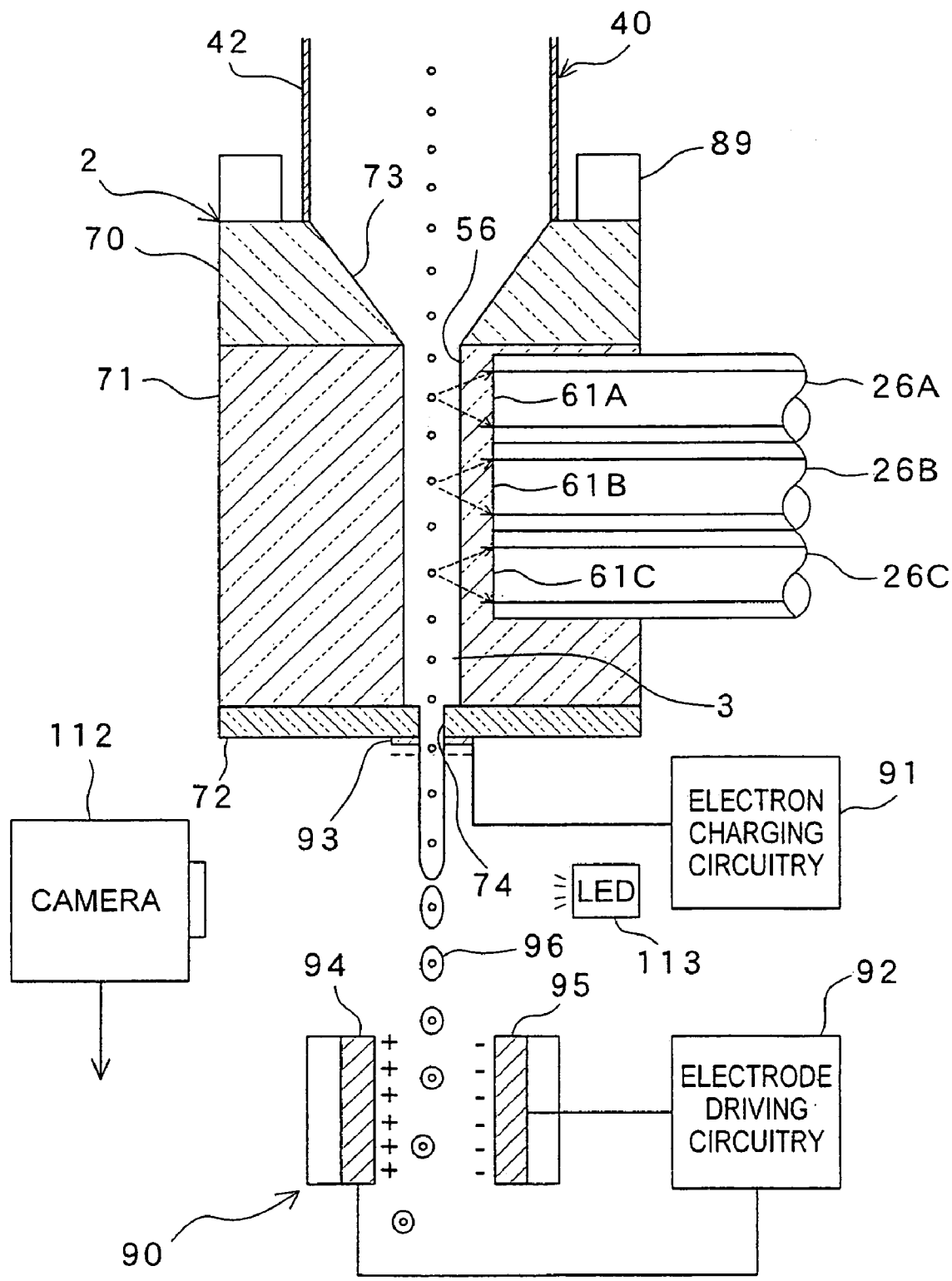
FIG. 4 is an enlarged cross sectional view of a detection flow path of the system of FIG. 1 and a portion of fiber optics arranged adjacent thereto.

As shown in the enlarged views of FIGS. 3, 4, the flow-path block 2 supports the 1st-3rd fiber optics 26A-26C for detecting the fluorescent/side-scattered light. Similar to a typical one of fiber optics, each of the fiber optics 26A-26C has a core for guiding light and a cladding layer surrounding the core. One ends 61A-61C of the 1st-3rd fiber optics 26A-26C are formed to be perpendicular to the central axis of the fiber optics 26A-26C, and also spaced away from the longitudinal wall 56 by a predetermined gap, so as to be arranged facing to the horizontal direction (Y-direction) perpendicular to the central axis of the vessel.

Referring to FIGS. 2 and 4, the flow-path block 2 supports an oscillation generator 89 which imparts oscillation on the flow-path block 2 in a vertical or radial direction to split (break off) the fluid ejected from the bottom orifice 74 into the droplet each containing the cell. Preferably, a plurality of the oscillation generators 89 are symmetrically arranged around the small-diameter cylinder 42, and also the oscillation generator incorporates a piezoelectric actuator (PZT).

As illustrated in FIG. 4, the flow cytometer 1 also includes a sorting device 90 for extracting particular groups of the particles. The sorting device 90 includes an electron charging circuitry 91 and an electrode driving circuitry (power source circuitry) 92. The electron charging circuitry 91 is connected with a charging electrode 93 that contacts the fluid ejected from the orifice 74. The electrode driving circuitry 92 is connected with a pair of conductive electrodes (deflection plate) 94, 95 that are provide beneath the orifice 74 on both side of the fluid ejected from the orifice. It should be noted that the location of the charging electrode 93 is not limited thereto, as long as it contacts the fluid running through the path flow 3 in the flow-path block 2.

III. Basic Operation:

According to the flow cytometer so structured, as shown in FIG. 2, the sheath fluid supplied from the sheath-fluid source 45 moves downwardly inside the vessel 40. The amount of the sheath fluid supplied per unit time is determined so that the sheath flow moves in a laminar flow around the central axis of the vessel 40. In the meanwhile, the suspension fluid supplied from the suspension-fluid source 48 is guided via the suspension-fluid tube 49 to the center of the sheath flow running as the laminar flow. This allows the sheath flow in the cylindrical laminar flow to surround the suspension fluid and to encompass each of particles running one-by-one through the central axis of the vessel 40 in a precise and discrete manner. Then, the suspension fluid and the sheath fluid are accelerated in the taper member 43 to the small-diameter cylinder 42, and again accelerated in the tapered flow path 73 of the flow-path block 2 to the flow path 3.

As illustrated in FIG. 3, when the 1st-3rd laser beams 8A-8C are irradiated onto the particles passing through the flow path 3, the forward-scattered light and the fluorescent/side-scattered light emanate from the particles. The forward-scattered light. 59 passes out of the flow-path block 2 through the wall surface 58 provided in a direction of extension of the 1st-3rd laser beams 8A-8C, which is detected by the first detecting apparatus 21. Also, the fluorescent/side-scattered light 60 of the 1st-3rd laser beams 8A-8C are collected into the 1st-3rd fiber optics 26A-26C, and detected by the second detecting apparatus 25.

As shown in FIG. 4, the sheath fluid passing through the flow path 3 is jet-ejected from the orifice 74. The oscillation imparted from the oscillation generator 89 to the small-diameter cylinder 42 of the vessel 40 causes the ejected sheath fluid to be a plurality of droplets, each of which contains the particle. In particular, according to the present embodiment, since the oscillation generator 89 is provided on the small-diameter cylinder 42 of the vessel 40, the oscillation generated by the oscillation generator 89 is efficiently transmitted to the mixed laminar flow, thereby properly splitting the laminar flow into a plurality of the droplets 96.

Each of the droplets 96 ejected from the orifice 74 is charged with positive or negative polarity by the electrode 93, of which potential is applied by the power supply circuitry 92. Thus, the polarity of the potential applied to the electrode 93 is determined based upon the biological characteristics (feature) of the particle that is detected by the signal processing apparatus 24. The charged particles 96 are deflected when falling between the electrode plates 94a, 95a, so that the particular type of the particles are selectively retrieved.

Figure 5:
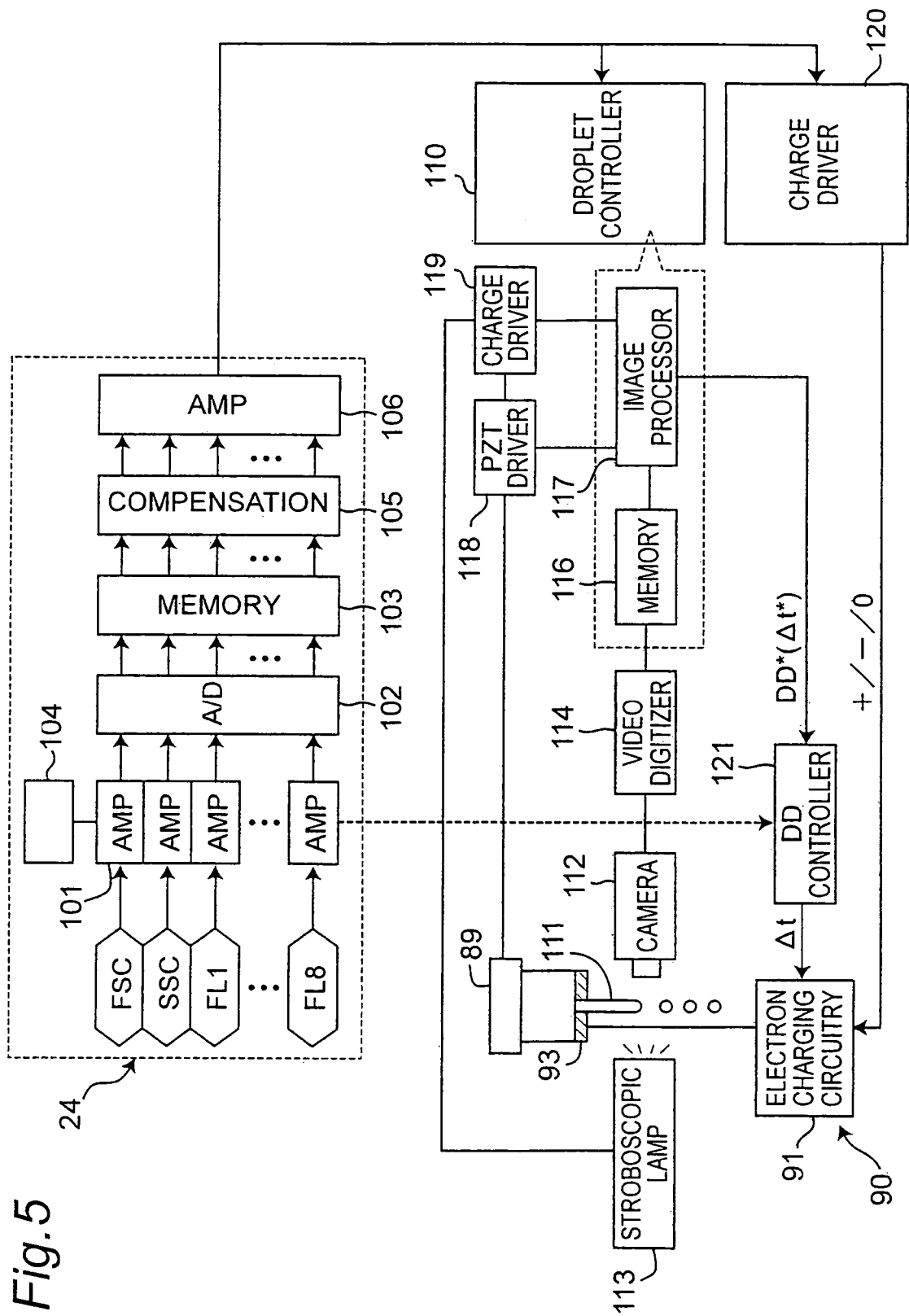
FIG. 5 is a circuit diagram of the system shown in FIG. 1.

IV. Control Circuitry:

FIG. 5 illustrates a circuit diagram of the signal processing apparatus 24 and the sorting device 90. As shown, the signal processing apparatus 24 includes a plurality of amplifiers 101 for amplifying signals (i.e., signals for the forward-scattered light, the side-scattered light, and the fluorescent light) detected by the optical detectors of the first and second detecting apparatuses 21, 25. An A/D (analog/digital) converter 102 is used for converting the amplified signals from analog signals into digital signals, which are then transmitted to and memorized in the memory 103.

As above, three of the fiber optics 26A-26C of the second detecting apparatus 25 are arranged at levels different from one another along the fluid flow running through the flow path 3. Thus, there is a predetermined time lag after the fluorescent/side-scattered light from a given particle is detected by one of the upstream fiber optics and before detected by another one of the downstream fiber optics. Thus, there is a predetermined time difference between the times when the signal from each fiber optical is input into the amplifier 101. According to the present embodiment, the amplifiers 101 connected with a timing controller 104 simultaneously outputs the signals for the given particle based upon the time difference determined by the timing controller 104. Also, the digital signals from the memory 103 are processed by a compensation circuitry 105 and an amplifier 106, and then output to the sorting device 90, which are used for controlling the droplets, i.e., sorting the particles.

The sorting device 90 includes a droplet controller 110 and a charge driver 120, which are connected with the signal processing apparatus 24.

The sorting device 90 is connected with a fixed camera (stationary imaging device) 112 for imaging the bottom end of the fluid flow ejected from the orifice 74 and the peripheral region thereof. A stroboscopic lamp 113 is secured on the side opposite to the stationary camera 112 while the sheath flow 110 is intervened therebetween, and flashes at a predetermined time period towards the sheath flow 110.

The output of the camera 112 is connected to a video digitizer (video capturing device) 114 for digitizing the image taken by the camera 112, in which the image (image signals) from the camera 112 is converted to digital signals by the video digitizer 114. The video digitizer 114 is connected to a memory 116 incorporated within the droplet controller 110, in which the image taken by the camera 112 is stored in the memory as image information. The memory 116 is connected to a image processor (central controller) 117 also incorporated within the droplet controller 110, in which the image information stored in the memory 116 is processed as will be described hereinafter. The central controller 117 is connected both with an oscillation generator driver 118 and a stroboscopic-lamp driver 119 for controlling operation of the oscillation generator 89 and the stroboscopic lamp 113, respectively. Also, the central controller 117 is connected with a drop-delay controller 121 for controlling the time (delay time) from the time when the particle passes through the detection point to the time just before the droplet containing the particle is split off the sheath flow 111. The drop-delay controller 121 is connected to the electron charging circuitry 91.

Figure 6:
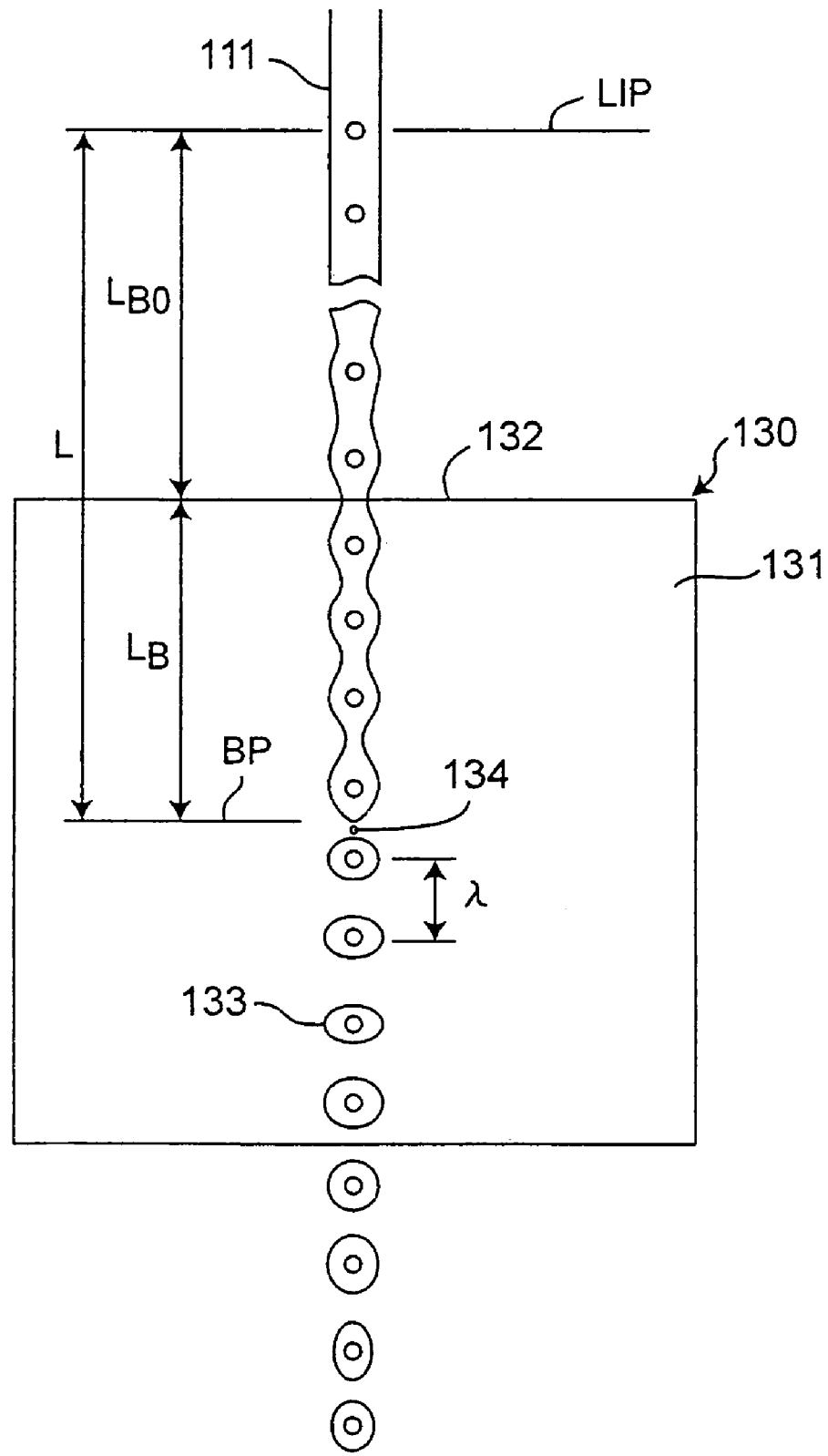
FIG. 6 is an enlarged elevational view of the sheath flow and the image taken by the camera.

The emission cycle t of the stroboscopic lamp 113 is fixed to the same as the cycle for applying the signals to the oscillation generator 89, that is, the oscillation cycle of the oscillation generator 89. Also, the emission cycle t is exactly consistent with the cycle that the droplets are formed. Therefore, the image of the sheath flow 111 taken by the stationary camera 112 has a constant shape as shown in FIG. 6.

In the meanwhile, the velocity v of the sheath flow 111 is represented as the following formula (1).

$$v \approx L/T \quad (1)$$

wherein L is a distance between the laser intercept point LIP (detection point) and the bottom point of the sheath flow (break-off point BP) and T is a time duration for the particle to move from the detection point LIP to the break-off point BP.

Also, the moving velocity of the particle (the falling velocity of the droplet) can be expressed with the emission cycle of the stroboscopic lamp 113 by the following formula (2).

$$v \approx \lambda/t \quad (2)$$

wherein λ is the interval between adjacent droplets and t is emission cycle of the stroboscopic lamp.

Therefore, from the above formulas (1) and (2), the following formula (3) is obtained.

$$L/T = \lambda/t \quad (3)$$

The formula (3) can be modified to the following formula (4).

$$T/t = L/\lambda \quad (4)$$

The term (T/t) in the formula (4) is the time duration for the particle to move from the detection point LIP to the break-off point BP that is divided by the emission cycle. Thus, the term corresponds to the number of the particles that can exist between the detection point LIP and the break-off point BP, which may be referred to as "drop delay DD". The drop delay DD may not always be an integer rather generally a fractional value. Therefore, the formula (4) can be modified as the following formula (5) with use of the drop delay DD.

$$DD = L/\lambda \quad (5)$$

FIG. 6 illustrates an image region of the camera 112 that is represented by a rectangular frame 130. As above, since the oscillation frequency of the oscillation generator 89 and the emission frequency of the stroboscopic lamp 113 are the exactly the same, the image of the sheath flow and the droplets split off the sheath flow, which is taken by the camera 112, are stationary as indicated, as long as other parameters such as the voltage of the pulse signal applied to the oscillation generator 89 are stable. Also, as illustrated in the drawing, the region taken by the camera 112 contains a portion of the sheath flow 111 including the break-off point BP and does not contain the detection point LIP so as to obtain a desirable resolution power for the image processing, as will be described hereinafter.

The distance $L_B$ between the break-off point BP and the upper end of the image can be measured, for example, by arranging an appropriate scale or an alternative dimensional reference along and beside the sheath flow 111, and comparing the size of the image (image pixels) with the scale.

Also, the distance $L_{B0}$ between the upper end of *the image and the detection point LIP can be calculated by the following calculation steps 1-3, as will be described hereinafter. Those calculation steps are automatically performed by the central controller 117.

Calculation Step 1:

The calculation step 1 is a step for calculating the time duration T while the particle moves from the detection point LIP to the break-off point BP. In the calculation step 1, an individual particle is controlled to run with a sufficient predetermined interval spaced from adjacent particles, and charged with electrons of a predetermined polarity (positive or negative polarity) from the charging electrode 93, while changing the delay time Δt'. Then, the particles that deflect in the intended direction are counted. The maximum number of the particles that deflect in the intended direction indicates the condition that the delay time Δt' corresponds to the moving time T. If the electron charging time deviates from this condition, the droplet and particles cannot properly be charged with the electrons preventing deflection thereof in the intended direction. Thus, when the delay time Δt' varies, the characteristics of the particle number (the number of counted particles) depending upon the delay time (Δt') is obtained, showing a situation of a quasi-Gaussian distribution (not shown). The delay time (Δt') having the peak of the quasi-Gaussian distribution corresponds to the moving time T, and the central controller 117 calculates the delay time (Δt'), which in turn is memorized in the memory 116 as the moving time T.

Figure 7:
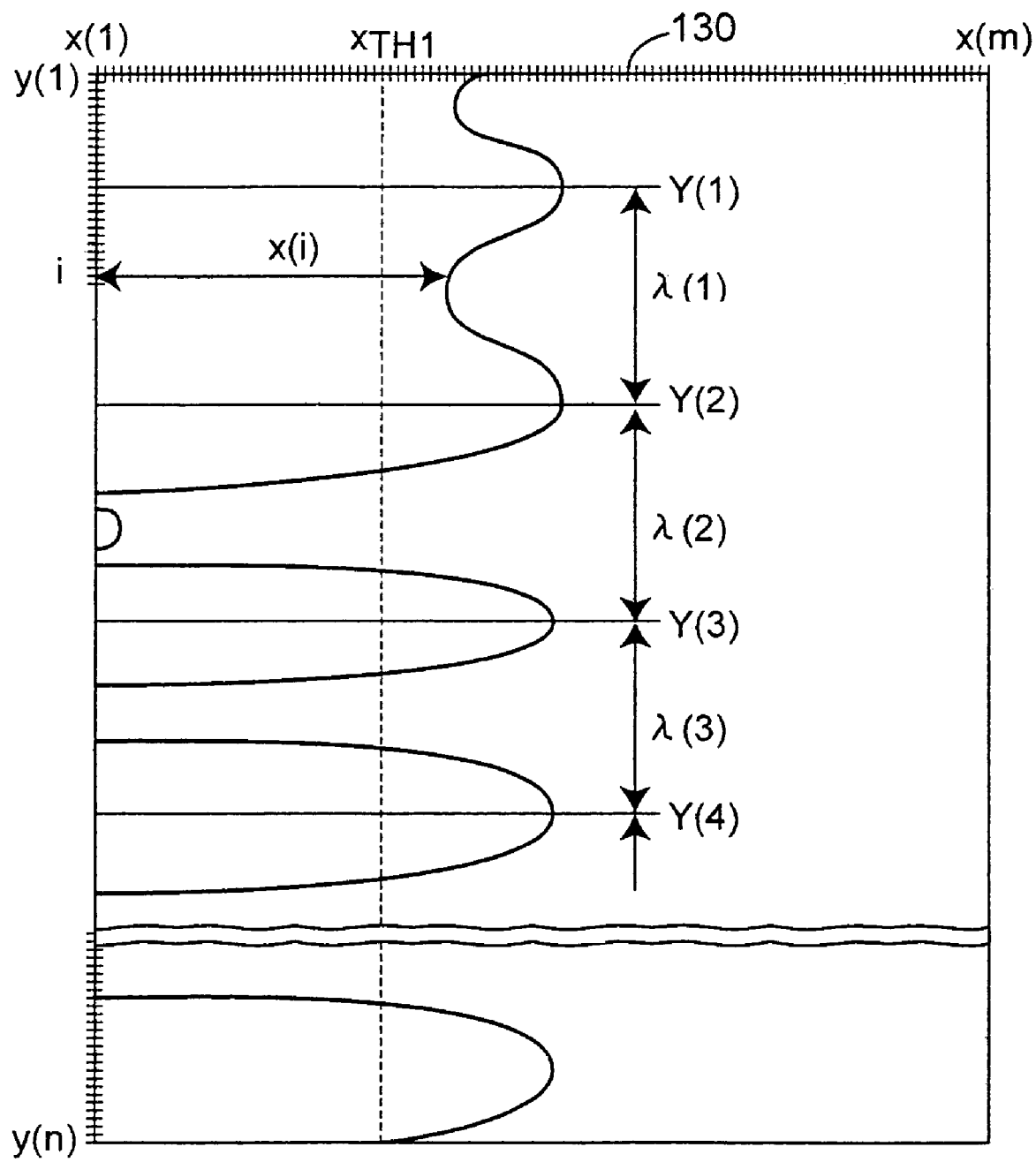
FIG. 7 is a chart of the image data after being processed, with the horizontal axis showing pixel numbers.

Calculation Step 2:

The calculation step 2 is a step for calculating an inter-particle average distance λ (which is equivalent to a gap between adjacent droplets) between the plural particles that may be found in a region between the detection point LIP and the break-off point BP. Referring to FIG. 6, for the droplets 133 being split off the sheath flow 111, the sheath flow 111 defines a plurality of large-diameter portions and small-diameter portions alternately formed with the constant gap, the inter-particle distance corresponds to the gap between the adjacent large-diameter portions (or the adjacent small-diameter portions). The central controller 117 distinguishes the sheath flow 111 from the background image by digitalizing the image data thereof. FIG. 7 illustrates the processed image data by digitalizing the image of the sheath flow 111 taken by the camera 112. In FIG. 7, the vertical and horizontal axes show the number (index) of the pixels for the height and horizontal distance of the image [y(i)] and [x(i)], respectively. The points Y(1), Y(2), Y(3), Y(4) indicate the height of the large-diameter portions (peaks) and the distance λ indicates the distance between the adjacent peaks (average distance).

Figure 9:
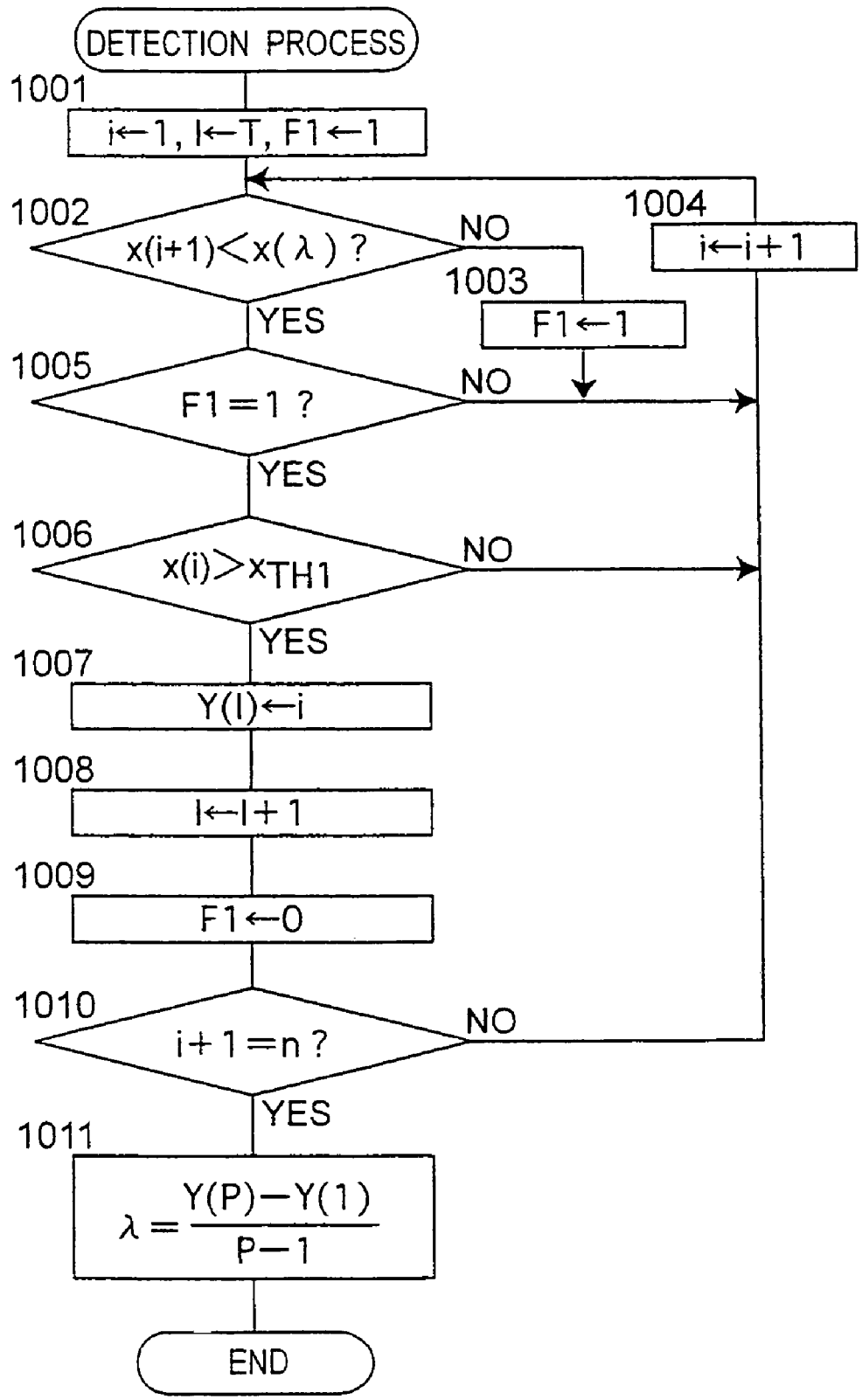
FIG. 9 is a flow chart for calculating X.

In particular, during the calculation step 2, as illustrated in the flow chart of FIG. 9, the central controller 117 initializes data required for subsequent processes, e.g., the row number of the Y-axis (i), the peak number (I), and the flag (F1) (step 1001). Then, the central controller 117 compares the pixel number x(i) of the sheath flow in the (i)th-row with the pixel number x(i+1) of the sheath flow in the (i+1)th-row (step 1002). If the pixel number x(i+1) of the (i+1)th-row is greater than the pixel number x(i) of the (i)th-row, i.e., the pixel number is increasing, then the flag (F1) is set to "1" (step 1003) and the row number (i) is incremented (step 1004). Meanwhile, if the pixel number x(i+1) of the (i+1)th-row is less than the pixel number x(i) of the (i)th-row, i.e., the pixel number is decreasing, then it is determined whether the flag (F1) is set to "1" or not (step 1005), thus, it is determined whether or not the pixel number that was increasing until the row number (i) has started decreasing from the row number (i+1). Next, it is determined whether the pixel number x(i) exceeds a predetermined value x(th1) (step 1006) (see FIG. 7), if the pixel number exceeds the predetermined value x(th1), then the row number (i) is set and memorized as Y(i) (step 1007), the peak number (I) is revised (step 1008), the flag (F1) is set to "0" (step 1009), and it is determined whether or not the row number (i+1) reaches the final row number (n) (step 1010). If the row number (i+1) does not reach the final row number, then the row number is incremented (step 1004) and the judge step 1002 is performed. When the row number (i+1) reaches the final row number (n), the inter-particle average distance (i.e., the distance λ) is calculated based upon the peak numbers Y(I) including Y(1), Y(2), Y(3), Y(4) obtained as above (step 1011). It should be noted that the predetermined value x(th1) is used for distinguishing a satellite drop (small droplet) as will be described hereinafter, from the large-diameter portions, and also is set to be greater than the size and the pixel number of the typically sized satellite drop.

Calculation Step 3:

The calculation step 3 is the calculation step, in which the central controller 117 calculates the distance $L_{BO}$ based upon the calculated time duration T and the distance λ. In particular, in the calculation step 3, the distance $L_{BO}$ is calculated in accordance with the formula (6) that is modified from the above-described formula (4).

$$T/t = (L_B + L_{BO})/\lambda$$

$$L_B + L_{BO} = (T/t) \cdot \lambda \quad (6)$$

$$L_{BO} = (T/t) \cdot \lambda - L_B$$

The time duration T, the distance λ, and the distance $L_B$ are calculated as above, and the stroboscopic emission cycle t is known. Therefore, the distance $L_{BO}$ can be calculated based upon the calculated values, and the distance L can be calculated based upon the calculated distance $L_{BO}$ and the distance $L_B$.

The central controller 117 determines the drop delay DD by assigning the calculated distances L and λ into the formula (5). The determined drop delay DD is memorized in the memory 116 and the drop-delay controller 121 as the reference value DD, which is used for controlling the drop delay as will be described hereinafter.

V. Sorting Control:

In the control process for sorting the particles, the droplet controller 110 and the charge driver 120 receives a signal (detection signal) from the signal processing apparatus 24, indicating that the detector detects the particles. Upon receipt of the detection signal, the droplet controller 110 drives the drop-delay controller 121 to activate the electron charging circuitry 91 after the delay time t corresponding to the memorized drop delay DD has passed, for charging the electrons with the fluid. The polarity of the charged electrons is determined by the charge driver 120 based upon the signals output from the signal processing apparatus 24. The electrons having the polarity determined by the charge driver 120 are injected to the fluid from the electron charging circuitry 91. Therefore, the droplet containing the detected particles is charged with the electrons having the polarity that corresponds to the biological feature detected for the particle, just before being split off the sheath flow 111. Also, the droplet is deflected during passing through the deflecting plates 94, 95 and sampled by the respective vessels (not shown).

Figure 10:
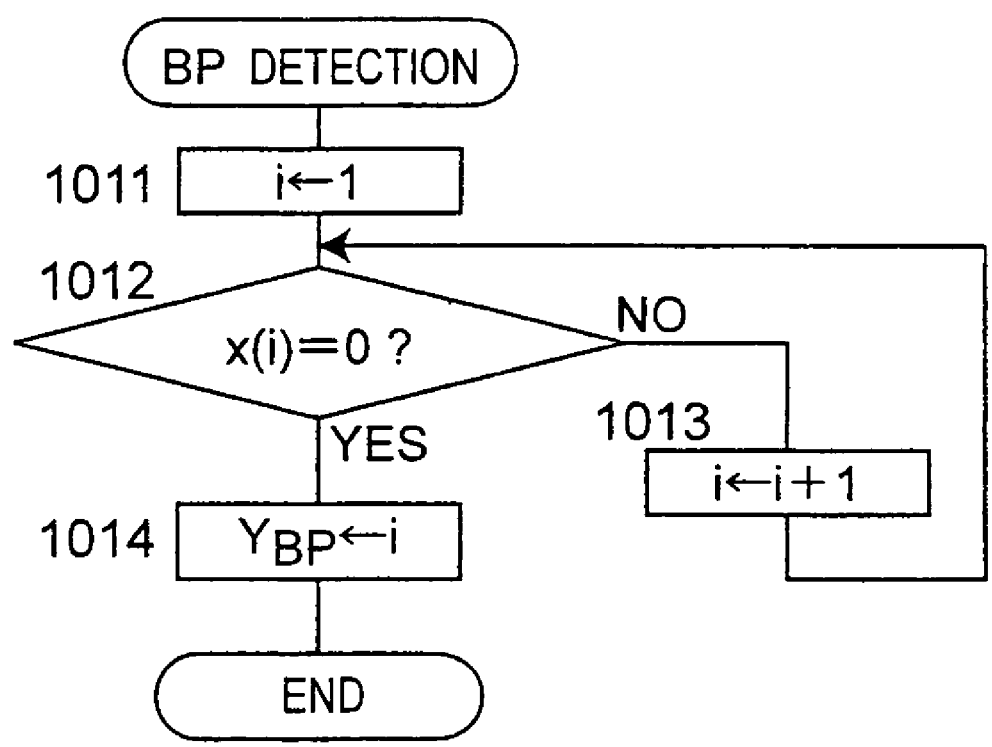
FIG. 10 is a flow chart for detecting the break-off point.

VI. Feedback Control (Drop-Delay Control):

The viscosity of the sheath fluid used by the flow cytometer 1 may vary in accordance with circumstance (e.g., temperature). When the viscosity of the sheath fluid varies, the position of the break-off point BP vertically shifts and also the time prior to formation of the droplet varies. The droplet controller 110 uses the image taken by the camera 112 for calculating the distance $L_B^*$ between the break-off point and the upper end of the image. This calculation may be made by arranging a scale or an alternative dimensional reference along and beside the sheath flow 111, and by comparing the distance $L_B^*$ with the size (pixel numbers) of the dimensional reference in the image taken by the camera. In particular, as illustrated in FIG. 10, the droplet controller 110 sets the row number (i) as "1 (one)" at the beginning (step 1011) and determines whether the pixel number x(i) is "0 (zero)" (step 1012). If the pixel number x(i) is not "0 (zero)", then the row number (i) is incremented (step 1013) for further determination (step 1012). If the pixel number x(i) is determined to be "0 (zero)", then the row number (i) is set to be $Y_{BP}$ (see FIG. 8) to calculate the distance $L_B^*$ in accordance with the $Y_{BP}$ and the dimensional reference.

Next, the droplet controller 110 calculates the interval λ* based upon the image taken by the camera 112. The calculation steps of the inter-particle interval are similar to the above calculation steps.

Subsequently, the droplet controller 110 calculates a new drop delay DD* based upon the calculated distance $L_B$* and interval λ* in accordance with the following formula (7) modified from the formula (5).

$$DD^* = (L_B^* + L_{B0})/\lambda^* \tag{7}$$

Using the new drop delay DD* calculated as above, the droplet controller 110 adjusts the time (delay time Δt) when the liquid is charged with electrons. As clearly indicated in the formula (7), $L_B^* + L_{B0}$ is a characteristic value of length, therefore, even if the frequency for forming the droplet and the pressure for supplying the sheath fluid vary, the drop delay DD can precisely be determined. Consequently, the high accuracy of the sorting can be maintained.

VII. Feedback Control (Voltage Control):

As illustrated in FIG. 6, when an individual droplet 133 is split off the sheath flow 111, a small satellite drop 134 that contains no particle is generated between the sheath flow 111 and the droplet 133. The figure illustrates the ideal condition where the satellite drop is separated from and independent upon the droplet 133, and it is the most preferable to inject electrons into the sheath flow 111 in the ideal condition. The droplet controller 110 monitors the condition of the satellite drop 134 on the binary data processed with the image taken by the camera 112, and controls the voltage across the oscillation generator 89 to adjust the amplitude of oscillation generated by the oscillation generator 89.

Figure 8:
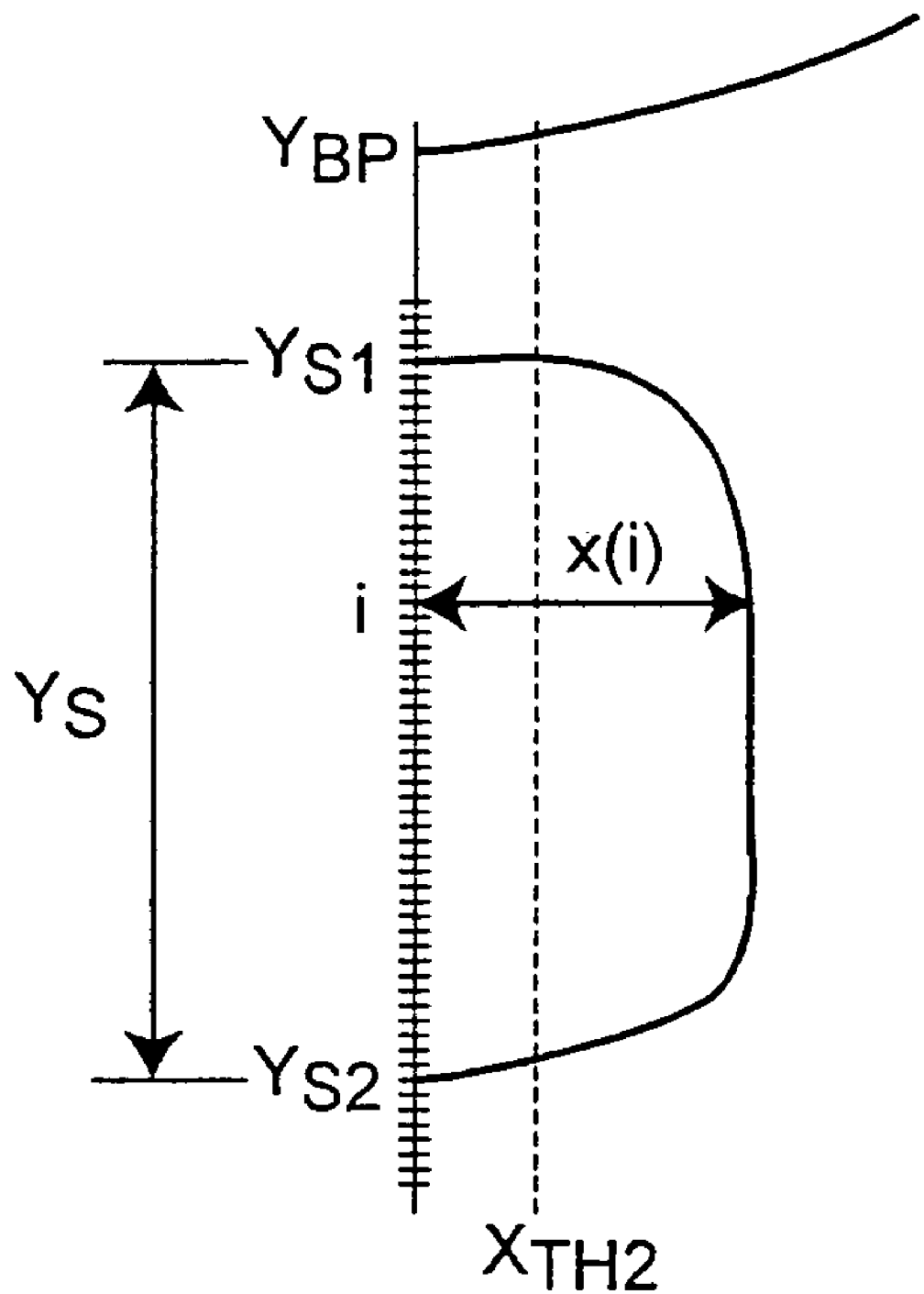
FIG. 8 is a chart having a horizontal axis of the pixel number for a satellite drop.
Figure 11:
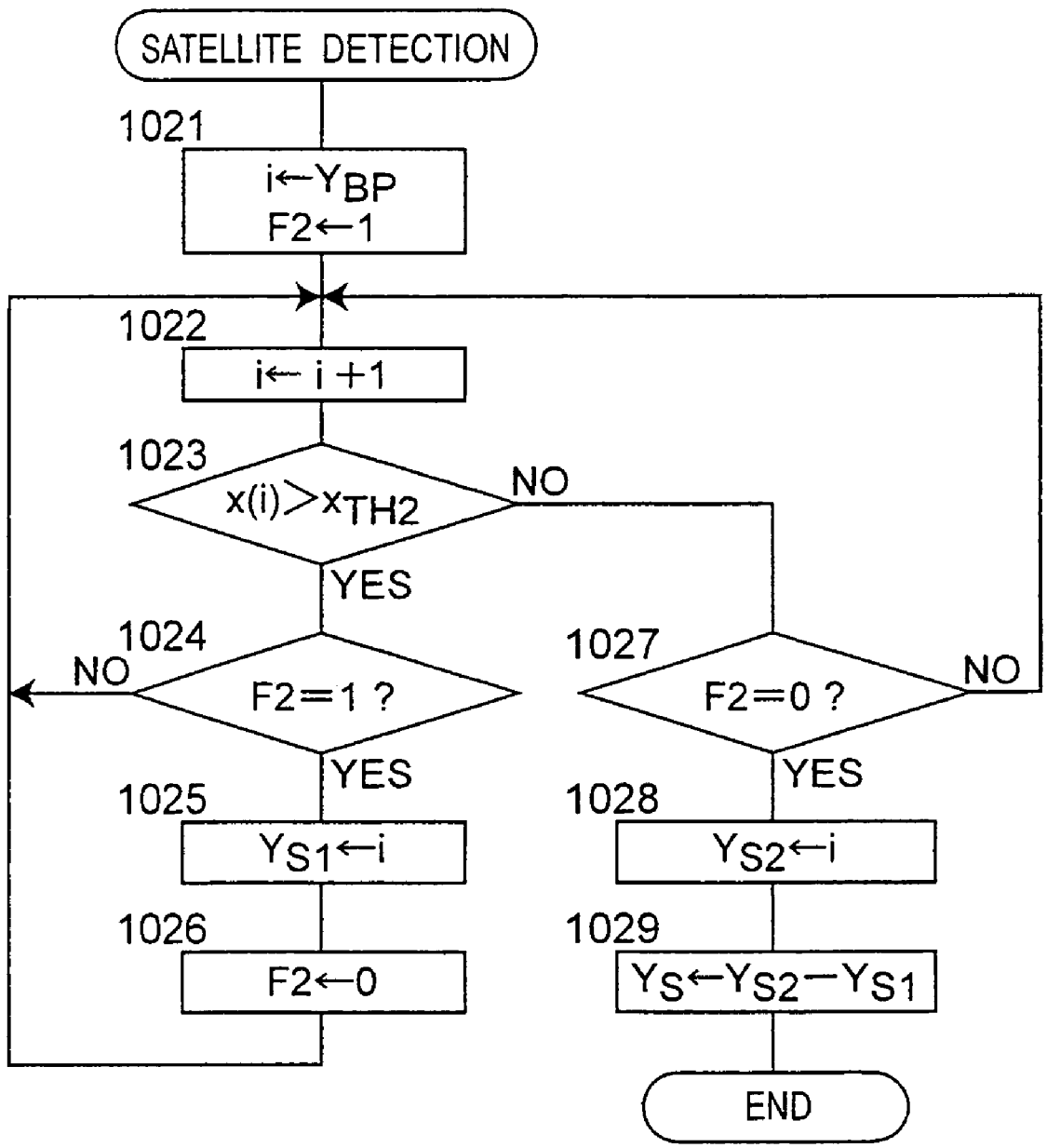
FIG. 11 is a flow chart for detecting the size of the satellite drop.

In particular, as illustrated in FIG. 11, the droplet controller 110 assigns the row number (i) with one for the break-off point BP and sets the flag F2 as "1 (one)" (step 1021). Next, the droplet controller 110 increments the row number to determine whether the pixel number x(i) for the row number (i) beneath the break-off point BP is exceeding a predetermined threshold value x(th2) (step 1023, see FIG. 8). When the pixel number x(i) is not exceeding a predetermined threshold value x(th2), it is determined whether the flag F2 is set as "0 (zero)" or not (step 1027). As above, the break-off point causes the pixel number x(i) to be "0(zero)". Therefore, as shown in FIG. 8, since several row numbers following the break-off point do not provide the pixel number x(i) with the threshold value x(th2), the steps 1022, 1023, 1027 are repeated. However, when the pixel number x(i) is exceeding the predetermined threshold value x(th2) (step 1023), it is determined whether the flag F2 is set as "1 (one)" or not (step 1024). When the pixel number x(i) is exceeding the predetermined threshold value x(th2) and if the flag F2 maintains the initial state (flag F2 =1), the row number (i) is set to be the row number YS1 of the upper end of the satellite drop (step 1025) and the flag F2 is switched to be "0 (zero)" (step 1026). Once the pixel number x(i) is exceeding the predetermined threshold value x(th2), such a situation is maintained for some time (see FIG. 8). Thus, the steps 1022, 1023, 1024 are repeated while the pixel number x(i) is exceeding the predetermined threshold value x(th2). When the row number (i) is close to the bottom end of the satellite drop, the pixel number x(i) is less than the predetermined value x(th2) (step 1023). Thus, the step is advanced from the step 1022 to the step 1027, and it is determined whether the flag F2 is set to be "0 (zero)". In this context, the flag F2 is set to be "0 (zero)" at step 1026. Thus, the row number (i) is set to be the row number YS2 of the lower end of the satellite drop (step 1028). Then, the pixel numbers YS from the upper end to the lower end of the satellite drop is calculated by subtracting the row number YS2 of the lower end from the row number YS1 of the upper end of the satellite drop (step 1028). The droplet controller 110 calculates the length of the satellite drop 134 based upon the pixel numbers YS. Next, the droplet controller 110 compares the calculated length YS of the satellite drop 134 with one of reference length $Y_{ref}$ and controls the voltage applied by the oscillation generator driver 118 across the oscillation generator 89 so that the length of the satellite drop is maintained. Instead of the length of the satellite drop, the droplet controller 110 may calculate and control area (size) of the image shown in FIG. 8 expressed in the following formula (8).

$$A = \sum_{YS1}^{YS2} x(i) \tag{8}$$

As above, since the flow cytometer 1 feedbacks the image data taken by the camera 112 to the voltage applied to the oscillation generator 89, an ideal shape-of the sheath flow can be defined at a predetermined position in stable and automatic manners. Also, the image taken by the camera 112 is used for controlling the drop delay DD (delay time Δt), so that the particles are precisely sorted.

Figure 12:
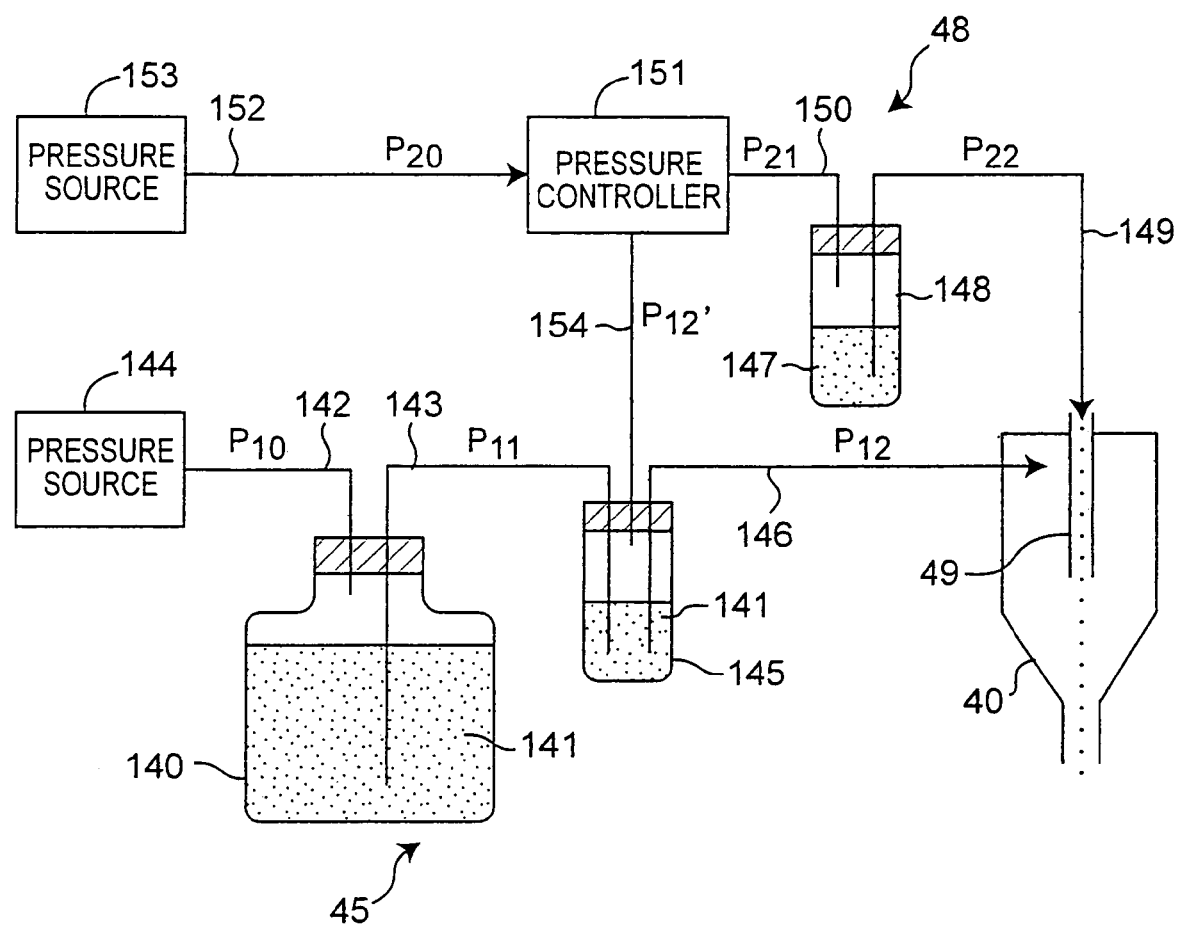
FIG. 12 is a schematic view illustrating the system for supplying the vessel with the sample fluid and the sheath fluid.

VIII. Suspension/Sheath Fluid Sources:

FIG. 12 illustrates the details of a sheath fluid source 45 and a suspension fluid source 48. As shown, the sheath fluid source 45 includes a sheath fluid container 140, in which the sheath fluid 141 is received. There are two tubes 142, 143 connected to the sheath fluid container 140. One tube 142 has one end connected to the upper closed space of the sheath fluid 141 and the other end connected to the pressure source 144. Also, the other tube 143 has one end immersed into the sheath fluid and the other end connected to a buffer container 145. The buffer container 145 has volume much smaller than that of the sheath fluid container 140 and is adapted for receiving the sheath fluid 141 supplied from the sheath fluid container 140 via the tube 143. The buffer container 145 is connected to a vessel 40 via another tube 146. As shown, the ends of the tubes 143, 146 are immersed into the sheath fluid 141 received in the buffer container 145.

The suspension fluid source 48 includes a sample container 148 for receiving the sample fluid 147 suspending the biological particles (cells or chromosome). A sample tube 149 is provided, which includes one end immersed into the sample fluid 147 in the sample container 148 and the other end connected to a sheath tube 49. Another tube 150 is provided, which includes one end connected to the upper closed space of the sample fluid 147 received in the sample container 148 and the other end connected to the pressure modulator 151, which is also connected to a pressure source 153 through another tube 152. Further, the pressure modulator 151 is also connected to the upper closed space of the buffer container 145 via a tube 154.

According to the system so structured, in the sheath fluid source 45, the sheath fluid 141 received in the sheath fluid container 140 is pressurized by the pressure P10 applied by the pressure source 10 via the tube 142, and supplied via the tube 143 to the buffer container at the pressure P11. Also, the sheath fluid 141 received in the buffer container 145 is supplied via the tube 146 to the vessel at the pressure P12. Meanwhile, in the suspension fluid source 48, the pressure P20 supplied by the pressure source 153 is modulated by the pressure modulator 151, so that the modulated pressure P21 is supplied to the upper closed space of the sample container 148. To this result, the sample fluid 147 in the sample container 148 is supplied to the sheath tube 49 via the tube 149 at a predetermined pressure P22. In order for the sample fluid 147 streaming from the sheath tube 49 not to be disturbed by the sheath fluid 147, the pressure P22 of he sample fluid 147 is modulated to be greater than the pressure P12 of the sheath fluid 141 by a predetermined pressure difference ΔP.

In particular, in the embodiment, the pressure P10, P11, P12 in the tubes 142, 143, 146 in the sheath fluid source 45 are substantially the same as one another. On the other hand, the pressure in the tubes 150, 149 in the suspension fluid source 48 and downstream the pressure modulator 151 is also substantially the same to each other. The pressure modulator 151 refers the internal pressure P12' of the buffer container 145 that is substantially the same as the pressure P11, P12, and adds the required pressure difference ΔP to the internal pressure P12', for realizing the pressure P21 from the pressure modulator 151.

In the embodiment, the volume of the sheath fluid container 145 and the buffer container 148 is set to be about one-tenth through about one thousandth, preferably one over five-hundredth of the volume of the sheath fluid container 140. Therefore, even when the level of the sheath fluid container 145 is lowered by consuming the sheath fluid 141, the pressure difference between the sheath fluid 141 and the sample fluid 147 can be maintained in the stable manner, in comparison with the case where no buffer container is provided.

Figure 13:
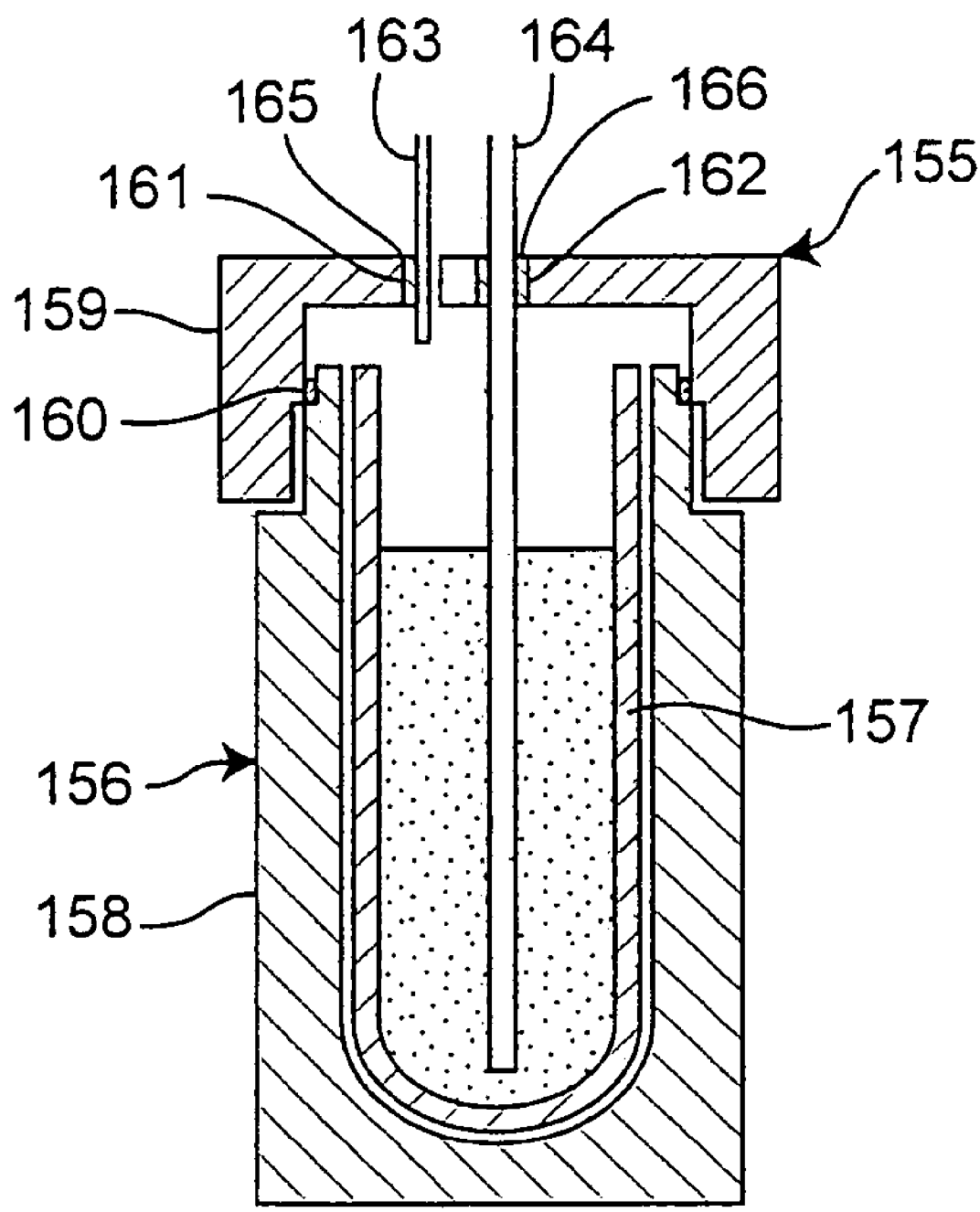
FIG. 13 is a cross sectional view of the container of the sample fluid or sheath fluid.

IX. Containers:

A container shown in FIG. 13 is preferably adapted for at least one of the sheath fluid container 145 of the sheath fluid source 45 and the sample container 148 of the suspension fluid source 48. The container of FIG. 13 includes an outer container 156 and an inner container 157. The outer container 156 may be formed of material such as metal and plastic having relatively high rigidity. The inner container 157 may be made of material such as glass. The outer container 156 includes a container body 158 for receiving the inner container 157 and a lid 15 that can be hermetically and detachably mounted on the upper opening of the container body 158. A mechanism for mounting the lid 159 onto the container body 158 preferably uses a conventional screw mechanism. Also, it is preferable that an O-ring is provided between the lid 159 and the container body 158 for sealing therebetween. The lid 159 includes a plurality of through-holes 161, 162 for insertion of the tubes 163, 164, and a plurality of annular resilient member 165, 166 of material such as rubber for sealing the circumstance of the tubes, so that the fluid (e.g., the sheath fluid or the sample fluid) can be supplied into the inner container 157 and the fluid contained therein can be pressurized. Adapting the container so structured for the sheath fluid container 145 and the sample container 148 allows the pressure in the outer container 156 to be maintained at a predetermined pressure for supplying the sample fluid in a stable manner, even when the pressure is added in the internal space defined by the outer container 156 formed of material having relatively high rigidity, and even if there is a crack in the inner container 157 made of generally fragile material such as plastic. In the sample container, the sample fluid has to be agitated by periodical oscillation to prevent the biological particles from being agglomerated. However, when the container 155 is adapted for the sample container, there is no problem that the periodical oscillation breaks the container since the outer container 156 is formed of material having relatively high rigidity. In the above embodiment, while the lid has the through-holes 161, 162 for insertion of the tubes 163, 164, the tubes may be fixed on the lid and have both ends (ends inside and outside the lid) which are connected with another tubes, respectively.

Figure 14:
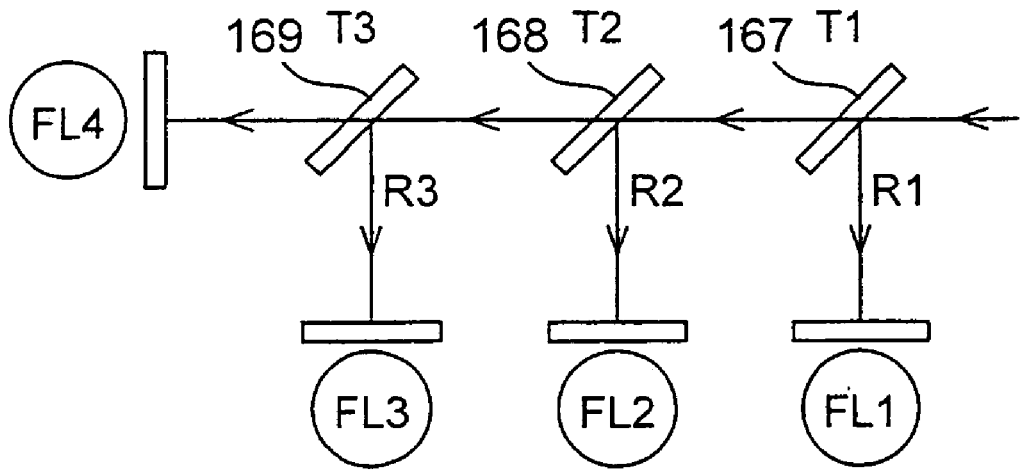
FIG. 14 is a schematic view illustrating arrangement of splitting filters of the detection apparatus.
Figure 15:
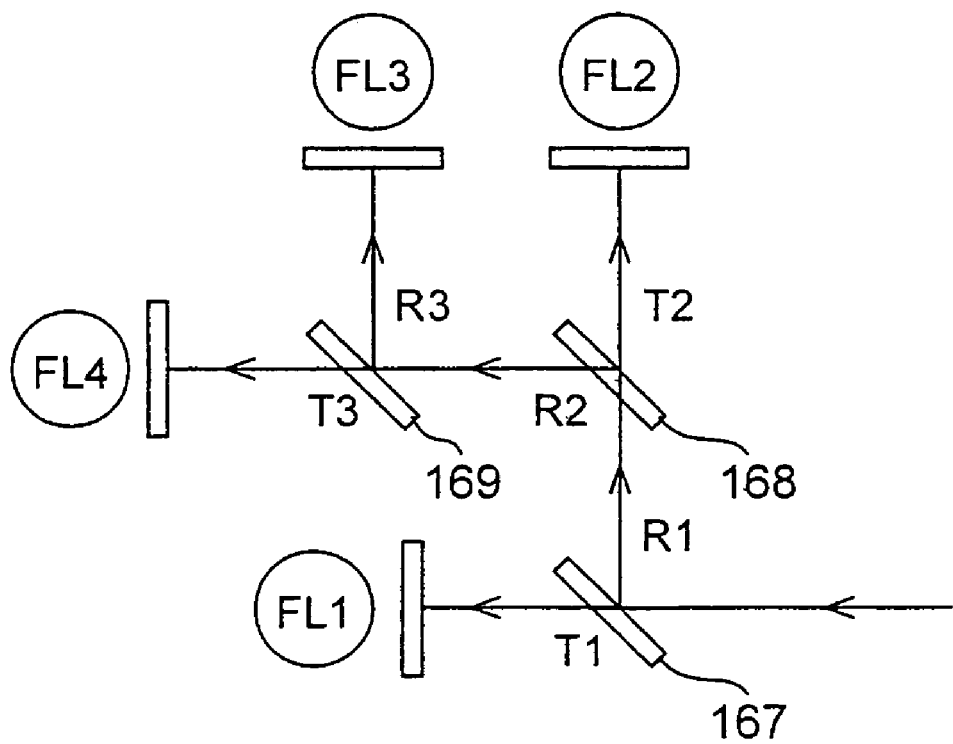
FIG. 15 is a schematic view illustrating preferable arrangement of splitting filters of the detection apparatus.

X. Arrangement of Splitting Filters:

In the flow cytometer 1, a dichroic mirror is typically used for the splitting filters 30A-30C. In general, the dichroic mirror has characteristics that the reflectance is greater than the transmissivity. For instance, the reflectance R is about 0.9 and the transmissivity is about 0.8. Therefore, for example, when three of the dichroic mirrors 167, 168, 169 are arranged in series as illustrated in FIG. 14 to detect the beam at the detectors FL1-FL4, as the incident beam has intensity of 1 (one), the relative beam intensity reflecting at and transmitting through the last splitting filter 169 are reduced to 0576 (0.8×0.8×0.9) and 0.512 (0.8×0.8×0.8), respectively. On the other hand, three of the dichroic mirrors 167, 168, 169 are arranged as illustrated in FIG. 15, the relative beam intensity reflecting at and transmitting through the last splitting filter 169 are 0.729 (0.9×0.9×0.9) and 0.648 (0.9×0.9×0.8), respectively, which increase the beam intensity for detection when comparing the arrangement of FIG. 14, thereby improving the detection sensibility of the detecting apparatus 25.

The invention claimed is:

1. A system for sorting a biological particle in accordance with biological information thereof, comprising:
   a path-defining structure which defines a liquid flow arranging a plurality of biological particles at a predetermined interval therein, and ejects the flow to form a droplet containing the biological particle;
   an irradiator for irradiating light onto the biological particle contained in the flow;
   an optical detector for detecting the light from the biological particle at a detection point;
   a stationary imaging device for imaging the flow and a droplet split off the flow in an image region having an upstream end that is spaced downstream from the detection point by a constant first distance;
   means for calculating, based upon the image taken by the imaging device, a second distance from the upstream end of the image region to a break-off point of the flow, and a droplet interval between adjacent droplets split off the flow, thereby calculating a time that the particle moves from the detection point to the break-off point, based upon the first and second distances and the droplet interval;
   means for providing the flow with electrons of a predetermined polarity depending upon the feature of the biological particle, when the calculated time passes after the optical detector detects the light from the biological particle.

2. The system according to claim 1, further comprising:
   a processor for collecting biological information on the biological particle from the light detected by the optical detector;
   means for providing the flow with electrons of a predetermined polarity depending upon the biological information on the biological particle processed by the processor, when the calculated time passes after the optical detector detects the light from the biological particle; and
   means for deflecting a falling direction of the droplet containing the biological particle with use of the electrons provided with the biological particle.

3. A process for sorting a biological particle, including:
   defining a liquid flow containing a biological particle;
   irradiating light onto the biological particle contained in the liquid flow;

detecting the light from the biological particle at a detection point;

collecting information on the biological particle based upon the detected light;

imaging the flow and a droplet split off the flow in an image region having an upstream end that is spaced downstream from the detection point by a constant first distance;

calculating, based upon the image of the flow, a second distance from the upstream end of the image region to a break-off point of the flow, and a droplet interval between adjacent droplets split off the flow;

calculating a time that the particle moves from the detection point, to the break-off point, with use of the first and second distances and the droplet interval;

injecting electrons to the flow based upon the information on the biological particle, when the calculated time passes after the light from the biological particle is detected; and sorting the droplet split off the flow in accordance with the injected electrons.

4. The system according to claim 1, wherein the irradiator irradiates the light onto the flow running through the path-defining structure.

5. The system according to claim 1, wherein the second distance is calculated by comparing the dimensional reference arranged along and beside the flow with a pixel number on the taken image.

6. The process according to claim 3, wherein the irradiating step includes irradiating the light onto the flow running through a path-defining structure.

7. The process according to claim 3, wherein the calculating step for calculating the second distance includes comparing the dimensional reference arranged along and beside the flow with a pixel number on the taken image.

* * * * *